United States Patent
Blakemore et al.

(10) Patent No.: US 6,596,900 B2
(45) Date of Patent: Jul. 22, 2003

(54) FUSED BICYCLIC OR TRICYCLIC AMINO ACIDS

(75) Inventors: David Clive Blakemore, Sandwich (GB); Justin Stephen Bryans, Sandwich (GB); Sophie Caroline Williams, Sandwich (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/124,210

(22) Filed: Apr. 16, 2002

(65) Prior Publication Data

US 2003/0078300 A1 Apr. 24, 2003

(30) Foreign Application Priority Data

Apr. 19, 2001 (GB) .............................................. 0109635
Oct. 26, 2001 (GB) .............................................. 0125807

(51) Int. Cl.⁷ .............................................. C07C 61/12
(52) U.S. Cl. ...................................... 562/501; 514/573
(58) Field of Search ........................... 562/501; 514/573

(56) References Cited

FOREIGN PATENT DOCUMENTS

| EP | 0074856 A | | 3/1983 |
|----|-----------|---|--------|
| EP | 1226820 | * | 7/2002 |
| JP | 05255169 A | | 10/1993 |
| WO | 9733859 A | | 9/1997 |
| WO | 9921824 A | | 5/1999 |
| WO | 9931075 A | | 6/1999 |
| WO | 9854193 A | | 12/2000 |
| WO | 0102978 | * | 4/2001 |
| WO | 0128978 A | | 4/2001 |
| WO | 0200209 A | | 1/2002 |

OTHER PUBLICATIONS

Synthesis of Cyclobutylideneacetic Esters Via Aluminum Chloride Promoted [2+2] Cycloadditions of Theyl 2,3–Butadienate to Olefins, TL, vol. 22, No. 21, pp. 1053–1959, 1981.

Lewis Acid Catalyzed Inter–and Intramolecular [2+] Cycloadditions of Conjugated Allenic Esters to Alkenes, *J. Org. Chem.*, 1986, vol. 51, pp. 3643–3652.

* cited by examiner

*Primary Examiner*—Paul J. Killos
(74) *Attorney, Agent, or Firm*—Peter C. Richardson; Paul H. Ginsburg; Israel Nissenbaum

(57) ABSTRACT

The compounds of the instant invention are bicyclic or tricyclic amino acids useful in the treatment of epilepsy, faintness attacks, hypokinesia, cranial disorders, neurodegenerative disorders, depression, anxiety, panic, pain, arthritis, neuropathological disorders, sleep disorders, visceral pain disorders, and gastrointestinal disorders. Processes for the preparation of the final products and intermediates useful in the process are included. Pharmaceutical compositions containing one or more of the compounds are also included.

9 Claims, No Drawings

FUSED BICYCLIC OR TRICYCLIC AMINO ACIDS

FIELD OF THE INVENTION

This invention relates to novel cyclic amino derivatives useful as pharmaceutical agents, to processes for their production, to pharmaceutical compositions containing them, and to their use for the treatment of the conditions set out below. It also relates to bicyclic and tricyclic ketones useful as intermediates in the production of the aforesaid compounds.

BACKGROUND TO THE INVENTION

Gabapentin (Neurontin®) is an anti-convulsant agent that is useful in the treatment of epilepsy and that has recently been shown to be a potential treatment for neurogenic pain. It is 1-(aminomethyl)-cyclohexylacetic acid of structural formula:

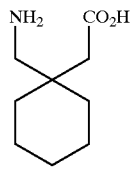

Gabapentin is one of a series of compounds of formula

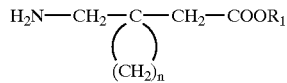

in which $R_1$ is hydrogen or a lower alkyl radical and n is 4, 5, or 6. These compounds are described U.S. Pat. No. 4,024,175 and its divisional U.S. Pat. No. 4,087,544. Their disclosed uses are: protection against thiosemicarbazide-induced cramp; protection against cardiazole cramp; the cerebral diseases, epilepsy, faintness attacks, hypokinesia, and cranial traumas; and improvement in cerebral functions. The compounds are useful in geriatric patients. The disclosures of the above two patents are hereby incorporated by reference.

WO 99/21824, whose disclosure is also incorporated by reference, discloses further cyclic amino acids that are useful in the treatment of epilepsy, faintness attacks, neurodegenerative disorders, depression, anxiety, panic, pain, neuropathological disorders, gastrointestinal disorders such as irritable bowel syndrome (IBS) and inflammation, especially arthritis. The compounds disclosed include those of the formula:

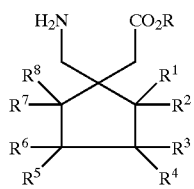

and salts thereof, in which: R is hydrogen or a lower alkyl; and $R^1$ to $R^8$ are each independently selected from hydrogen, straight or branched alkyl of from 1 to 6 carbons, phenyl, benzyl, fluorine, chlorine, bromine, hydroxy, hydroxymethyl, amino, aminomethyl, trifluoromethyl, $—CO_2H$, $—CO_2R^{14}$, $—CH_2CO_2H$, $—CH_2CO_2R^{15}$, $—OR^{15}$ wherein $R^{15}$ is a straight or branched alkyl of from 1 to 6 carbons, phenyl, or benzyl, $R^1$ to $R^8$ not being simultaneously hydrogen.

International Patent Application Publication No. WO0128978, corresponding to U.S. patent application Ser. No. 60/160725, describes a series of novel bicyclic amino acids, their pharmaceutically acceptable salts, and their prodrugs of formula:

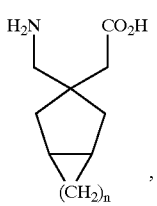

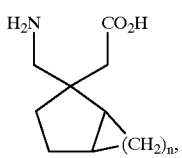

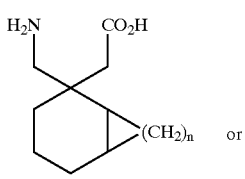

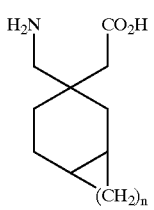

wherein n is an integer of from 1 to 4, where there are stereocentres, each center may be independently R or S, preferred compounds being those of Formulae I–IV above in which n is an integer of from 2 to 4. The compounds are disclosed as being useful in treating a variety of disorders including epilepsy, faintness attacks, hypokinesia, cranial disorders, neurodegenerative disorders, depression, anxiety, panic, pain, neuropathological disorders, and sleep disorders. Certain of the compounds disclosed in that patent have high activity as measured in a radioligand binding assay using [$^3$H]gabapentin and the $\alpha_2\delta$ subunit derived from porcine brain tissue (Gee N. S., Brown J. P., Dissanayake V. U. K., Offord J., Thurlow R., Woodruff G. N., *J. Biol. Chem.*, 1996;271:5879–5776). Results for some of the compounds are set out in the following table:

TABLE 1

| Compound | Structure | α₂δ binding affinity ($\mu$M) |
|---|---|---|
| (1α, 3α, 5α)(3-Aminomethyl-bicyclo[3.2.0]hept-3-yl)-acetic acid | | 0.038 |
| (+/−)-(1α, 5β)(3-Aminomethyl-bicyclo[3.2.0]hept-3-yl)-acetic acid | | 2.86 |
| ((1α, 3β, 5α)(3-Aminomethyl-bicyclo[3.2.0]hept-3-yl)-acetic acid | | 0.332 |

Patent application number EP 01400214.1 discloses the use of compounds of formula I to IV above for preventing and treatment of visceral pain, and gastrointestinal disorders.

SUMMARY OF THE INVENTION

Certain analogues of the above compounds which derived e.g. from 1-(aminomethyl)-cyclopentaneacetic acid by fusion of a 3- or 4-membered ring to the cyclopentane ring and which are substituted with one or more substituents exhibit similar high activity. Also, amino acids based on bicyclo[3.2.0]heptane, bicyclo[4.2.0]octane and bicyclo[5.2.0]nonane in which the amino and carboxyl moieties are attached to one of the atoms of the four-membered ring exhibit high activity.

The present invention provides bicyclic amino acid analogues and their derivatives, prodrugs, and pharmaceutically acceptable salts and solvates useful in the treatment of a variety of disorders including epilepsy, faintness attacks, hypokinesia, cranial disorders, neurodegenerative disorders, depression, anxiety, panic, pain, sleep disorders, osteoarthritis, rheumatoid arthritis, and neuropathological disorders. The compounds provided may also be useful in the treatment of visceral pain, functional bowel disorders such as gastro-esophageal reflux, dyspepsia, irritable bowel syndrome and functional abdominal pain syndrome, and inflammatory bowel diseases such as Crohn's disease, ileitis, and ulcerative colitis, and other types of visceral pain associated with dysmenorrhea, pelvic pain, cystitis and pancreatitis. They may also be used for the treatment of premenstrual syndrome. They are compounds of any of the general formulae below:

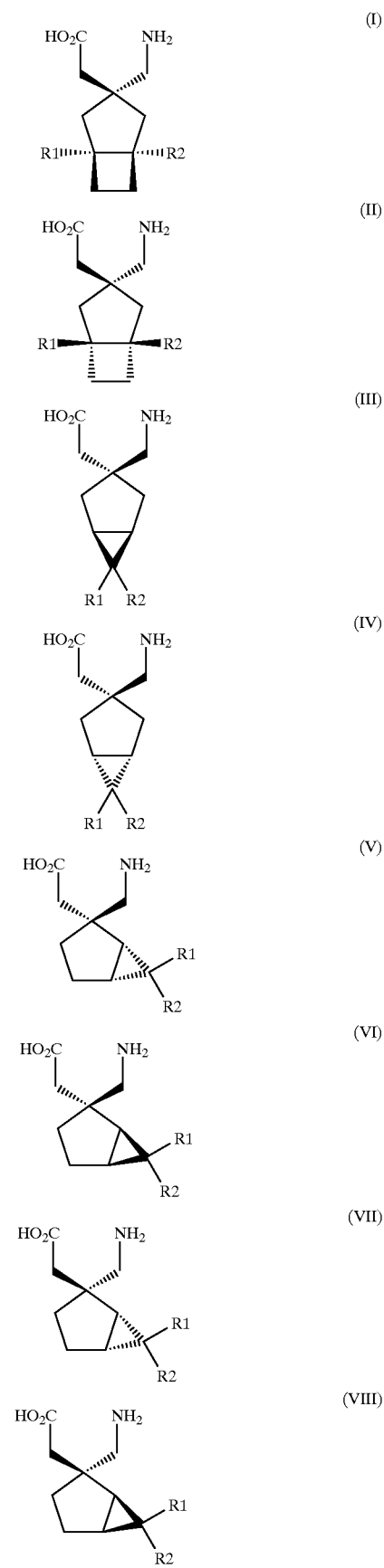

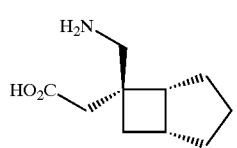
(IX)
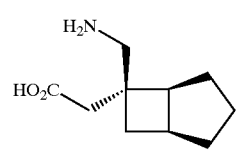
(X)
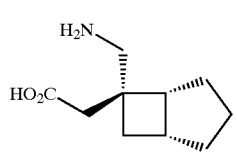
(XI)
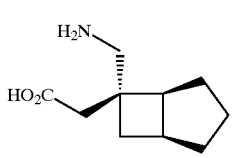
(XII)
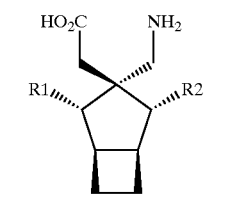
(XIII)
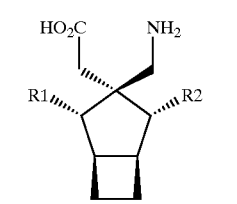
(XIV)
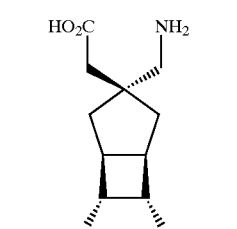
(XV)
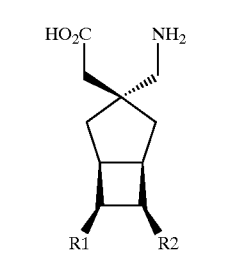
(XVI)
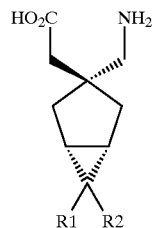
(XVII)
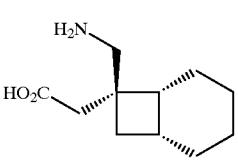
XVIII
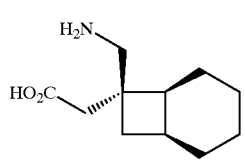
XIX
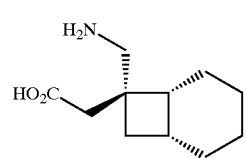
XX
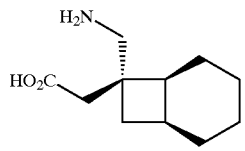
XXI
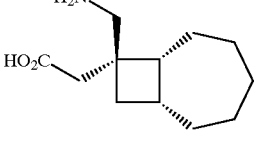
XXII
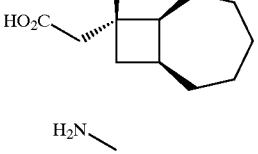
XXIII
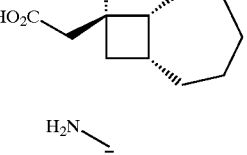
XXIV
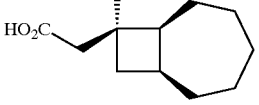
XXV wherein R¹ and R² are each independently selected from H, straight or branched alkyl of 1–6 carbon atoms, cycloalkyl of from 3–6 carbon atoms, phenyl and benzyl, subject to the proviso that, except in the case of a tricyclooctane compound of formula (XVII), R¹ and R² are not simultaneously hydrogen.

Suitable compounds (including salts, solvates and pro-drugs thereof) are:

((1R,5S)-3-Aminomethyl-1,5-dimethyl-bicyclo[3.2.0]hept-3-yl)-acetic acid;
((1S,5R)-3-Aminomethyl-1,5-dimethyl-bicyclo[3.2.0]hept-3-yl)-acetic acid;
((1R,5S)-3-Aminomethyl-6,6-dimethyl-bicyclo[3.1.0]hex-3-yl)-acetic acid;
((1S,5R)-3-Aminomethyl-6,6-dimethyl-bicyclo[3.1.0]hex-3-yl)-acetic acid;
((1S,2S,5R)-2-Aminomethyl-6,6-dimethyl-bicyclo[3.1.0]hex-2-yl)-acetic acid;
((1R,2S,5S)-2-Aminomethyl-6,6-dimethyl-bicyclo[3.1.0]hex-2-yl)-acetic acid;
((1S,2R,5R)-2-Aminomethyl-6,6-dimethyl-bicyclo[3.1.0]hex-2-yl)-acetic acid;
((1R,2R,5S)-2-Aminomethyl-6,6-dimethyl-bicyclo[3.1.0]hex-2-yl)-acetic acid;
((1R,5R,6S)-6-Aminomethyl-bicyclo[3.2.0]hept-6-yl)-acetic acid;
((1S,5S,6S)-6-Aminomethyl-bicyclo[3.2.0]hept-6-yl)-acetic acid;
((1R,5R,6R)-6-Aminomethyl-bicyclo[3.2.0]hept-6-yl)-acetic acid;
((1S,5S,6R)-6-Aminomethyl-bicyclo[3.2.0]hept-6-yl)-acetic acid;
cis-((1S,2R,4S,5R)-3-Aminomethyl-2,4-dimethyl-bicyclo[3.2.0]hept-3-yl)-acetic acid;
trans-((1S,2R,4S,5R)-3-Aminomethyl-2,4-dimethyl-bicyclo[3.2.0]hept-3-yl)-acetic acid;
((1S,5R,6S,7R)-3-Aminomethyl-6,7-dimethyl-bicyclo[3.2.0]hept-3-yl)-acetic acid;
((1S,5R,6R,7S)-3-Aminomethyl-6,7-dimethyl-bicyclo[3.2.0]hept-3-yl)-acetic acid;
((1R,2S,5 S)-7-Aminomethyl-3,3-dimethyl-tricyclo[3.3.0.0]oct-7-yl)-acetic acid;
((1R,6R,7S)-7-Aminomethyl-bicyclo[4.2.0]oct-7-yl)-acetic acid;
((1S,6S,7S)-7-Aminomethyl-bicyclo[4.2.0]oct-7-yl)-acetic acid;
((1R,6R,7R)-7-Aminomethyl-bicyclo[4.2.0]oct-7-yl)-acetic acid;
((1S,6S,7R)-7-Aminomethyl-bicyclo[4.2.0]oct-7-yl)-acetic acid;
((1R,7R,8S)-8-Aminomethyl-bicyclo[5.2.0]non-8-yl)-acetic acid;
((1S,7S,8S)-8-Aminomethyl-bicyclo[5.2.0]non-8-yl)-acetic acid;
((1R,7R,8R)-8-Aminomethyl-bicyclo[5.2.0]non-8-yl)-acetic acid; and
((1S,7S,8R)-8-Aminomethyl-bicyclo[5.2.0]non-8-yl)-acetic acid.

Preferred compounds (including salts, solvates and pro-drugs thereof) are:

[(1R,5R,6S)-6-(Aminomethyl)bicyclo[3.2.0]hept-6-yl] acetic acid;
[(1S,5S,6R)-6-(Aminomethyl)bicyclo[3.2.0]hept-6-yl] acetic acid;
[(1RS,5RS,6RS)-6-(Aminomethyl)bicyclo[3.2.0]hept-6-yl] acetic acid;
[(1RS,6RS,7SR)-7-(Aminomethyl)bicyclo[4.2.0]oct-7-yl] acetic acid; and
[(1RS,6RS,7RS)-7-(Aminomethyl)bicyclo[4.2.0]oct-7-yl] acetic acid.

A particularly preferred compound (including salts, solvates and pro-drugs thereof) is [(1R,5R,6S)-6-(Aminomethyl)bicyclo[3.2.0]hept-6-yl]acetic acid.

The present compounds can exist in unsolvated forms as well as solvated forms, including hydrated forms. In general, the solvated forms, including hydrated forms, which may contain isotopic substitutions (e.g. D2O, d6-acetone, d6-DMSO), are equivalent to unsolvated forms and are encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof. Separation of diastereoisomers or cis and trans isomers may be achieved by conventional techniques, e.g. by fractional crystallisation, chromatography or H.P.L.C. of a stereoisomeric mixture of a compound of the invention or a suitable salt or derivative thereof. An individual enantiomer of a compound of the invention may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

The present invention also includes all suitable isotopic variations of a compound of the invention or a pharmaceutically acceptable salt thereof. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that can be incorporated into compounds of the invention and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the compounds of the invention and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the compounds of the invention and pharmaceutically acceptable salts thereof of this invention can generally be prepared by conventional procedures such as by the illustrative methods or by the preparations described in the Examples and Preparations hereafter using appropriate isotopic variations of suitable reagents.

Since amino acids are amphoteric, pharmacologically compatible salts can be salts of appropriate non-toxic inorganic or organic acids or bases. Suitable acid addition salts are the hydrochloride/chloride, hydrobromide/bromide, hydroiodide/iodide, sulphate, bisulphate, nitrate, phosphate, hydrogen phosphate, acetate, fumarate, aspartate, besylate, bicarbonate/carbonate, camsylate, D and L-lactate, D and L-tartrate, edisylate, mesylate, malonate, orotate, gluceptate, methylsulphate, stearate, glucuronate, 2-napsylate, tosylate, hibenzate, nicotinate, isethionate, malate, maleate, citrate, gluconate, succinate, saccharate, benzoate, esylate, and pamoate salts. Suitable base salts are formed from bases which form non-toxic salts and examples are the sodium, potassium, aluminium, calcium, magnesium, zinc, choline, diolamine, olamine, arginine, glycine, tromethamine, benzathine, lysine, meglumine and diethylamine salts. Salts with quaternary ammonium ions can also be prepared with, for example, the tetramethyl-ammonium ion. The compounds of the invention may also be formed as a zwitterion.

A suitable salt of compounds of the present invention is the hydrochloride salt. For a review on suitable salts see Berge et al, J. Pharm. Sci., 66, 1–19, 1977.

Also included within the present scope of the compounds of the invention are polymorphs thereof.

Prodrugs of the above compounds are included in the scope of the instant invention. The effectiveness of an orally administered drug is dependent upon the drug's efficient transport across the mucosal epithelium and its stability in entero-hepatic circulation. Drugs that are effective after parenteral administration but less effective orally, or whose plasma half-life is considered too short, may be chemically modified into a prodrug form. A prodrug is a drug which has been chemically modified and may be biologically inactive at its site of action, but which may be degraded or modified by one or more enzymatic or other in vivo processes to the parent bioactive form. This chemically modified drug, or prodrug, should have a different pharmacokinetic profile to the parent, enabling easier absorption across the mucosal epithelium, better salt formulation and/or solubility, improved systemic stability (for an increase in plasma half-life, for example). These chemical modifications may be (1) Ester or amide derivatives which may be cleaved by, for example, esterases or lipases. For ester derivatives, the ester is derived from the carboxylic acid moiety of the drug molecule by known means. For amide derivatives, the amide may be derived from the carboxylic acid moiety or the amine moiety of the drug molecule by known means.

(2) Peptides which may be recognized by specific or non-specific proteinases. A peptide may be coupled to the drug molecule via amide bond formation with the amine or carboxylic acid moiety of the drug molecule by known means.

(3) Derivatives that accumulate at a site of action through membrane selection of a prodrug form or modified prodrug form.

(4) Any combination of 1 to 3.

It will further be appreciated by those skilled in the art that certain moieties known to those skilled in the art as "pro-moieties", for example as described in "Design of Prodrugs" by H Bundgaard (Elsevier) 1985, may be placed on appropriate functionalities when such functionalities are present in compounds of the invention also to form a "prodrug". Further, certain compounds of the invention may act as prodrugs of other compounds of the invention. All protected derivatives, and prodrugs, of the compounds of the invention are included within the scope of the invention.

Research has shown that the oral absorption of certain drugs may be increased by the preparation of "soft" quaternary salts. The quaternary salt is termed a "soft" quaternary salt since, unlike normal quaternary salts, e.g., R—N$^+$(CH$_3$)$_3$, it can release the active drug on hydrolysis. "Soft" quaternary salts have useful physical properties compared with the basic drug or its salts. Water solubility may be increased compared with other salts, such as the hydrochloride, but more important there may be an increased absorption of the drug from the intestine. Increased absorption is probably due to the fact that the "soft" quaternary salt has surfactant properties and is capable of forming micelles and unionized ion pairs with bile acids, etc., which are able to penetrate the intestinal epithelium more effectively. The prodrug, after absorption, is rapidly hydrolyzed with release of the active parent drug.

Aminoacyl-glycolic and -lactic esters are known as prodrugs of amino acids (Wermuth C. G., *Chemistry and Industry*, 1980:433–435). The carbonyl group of the amino acids can be esterified by known means. Prodrugs and soft drugs are known in the art (Palomino E., *Drugs of the Future*, 1990;15(4):361–368). The last two citations are hereby incorporated by reference.

The invention also relates to therapeutic use of the present compounds as agents for treating or relieving the symptoms of neurodegenerative disorders. Such neurodegenerative disorders include, for example, Alzheimer's disease, Huntington's disease, Parkinson's disease, and Amyotrophic Lateral Sclerosis. The present invention also covers treating neurodegenerative disorders termed acute brain injury. These include but are not limited to: stroke, head trauma, and asphyxia. Stroke refers to a cerebral vascular disease and may also be referred to as a cerebral vascular accident (CVA) and includes acute thromboembolic stroke. Stroke includes both focal and global ischemia. Also, included are transient cerebral ischemic attacks and other cerebral vascular problems accompanied by cerebral ischemia. These vascular disorders may occur in a patient undergoing carotid endarterectomy specifically or other cerebrovascular or vascular surgical procedures in general, or diagnostic vascular procedures including cerebral angiography and the like. Other incidents are head trauma, spinal cord trauma, or injury from general anoxia, hypoxia, hypoglycemia, hypotension as well as similar injuries seen during procedures from embole, hyperfusion, and hypoxia. The instant invention would be useful in a range of incidents, for example, during cardiac bypass surgery, in incidents of intracranial hemorrhage, in perinatal asphyxia, in cardiac arrest, and status epilepticus.

A skilled physician will be able to determine the appropriate situation in which subjects are susceptible to or at risk of, for example, stroke as well as suffering from stroke for administration by methods of the present invention.

The compounds of the invention are also useful for the treatment of acute and chronic pain. Acute pain is usually short-lived and is associated with hyperactivity of the sympathetic nervous system. Examples are postoperative pain, such as following a dental extraction, migraine, headache, trigeminal neuralgia and allodynia. Chronic pain is usually defined as pain persisting from 3 to 6 months and includes somatogenic pains and psychogenic pains. Examples of chronic pain include pain associated with musculo- skeletal disorders such as rheumatoid arthritis, osteoarthritis, ankylosing spondylitis, sero-negative (non-rheumatoid) arthropathies, non-articular rheumatism and peri-articular disorders, and pain associated with cancer, peripheral neuropathy and post-herpetic neuralgia. Other pain is nociceptive. Still other pain is caused by injury or infection of peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Neuropathic pain includes, but is not limited to, pain caused by nerve injury such as, for example, diabetic pain. Psychogenic pain is that which occurs without an organic origin such as low back pain, atypical facial pain, and chronic headache. Other types of pain are: inflammatory pain, osteoarthritic pain, trigeminal neuralgia, cancer pain, diabetic neuropathy, restless leg syndrome, acute :herpetic and postherpetic neuralgia, causalgia, brachial plexus avulsion, occipital neuralgia, gout, phantom limb, bum, and other forms of neuralgia, neuropathic and idiopathic pain syndrome.

The compounds of the invention are also expected to be useful in the treatment of depression. Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients'mood. These evaluations of mood are generally performed by a physician or quantified by a neuropsychologist using validated rating scales, such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in the Diagnostic and Statistical Manual of Mental Disorders (Fourth Edition) referred to as the DSM-IV-R manual published by the American Psychiatric Association, 1994.

The compounds of the invention are also expected to be useful in the treatment of visceral pain, and gastrointestinal disorders. The viscera encompasses the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders include the functional bowel disorders (FBD) and the inflammatory bowel diseases (IBD). These GI disorders include a wide range of disease states that are currently only moderately controlled, including—for FBD, gastro-esophageal reflux, dyspepsia, the irritable bowel syndrome (IBS) and functional abdominal pain syndrome (FAPS), and—for IBD, Crohn's disease, ileitis, and ulcerative colitis, and all regularly produce visceral pain. It has been shown recently in these pathologies, in particular the irritable bowel syndrome and dyspepsia, that the visceral pain threshold is decreased, indicating a visceral hypersensitivity. Other types of visceral pain include the pain associated with dysmenorrhea, pelvic pain, cystitis and pancreatitis.

Few drugs are known to act selectively upon GI disorder-associated hypersensitivity (Farthing M. J. (1998) *Drugs* 56:11–21). Available treatments of pain fall into two main categories: (1) nonsteroidal anti-inflammatory drugs, used to treat mild pain, but whose therapeutic use is limited by GI adverse effects (gastric erosion, peptic ulcer formation, inflammation of the duodenum and colon); (2) morphine and related opioids, used to treat moderate to severe pain but whose therapeutic use is limited by undesirable side effects including constipation, respiratory depression, tolerance, and abuse potential.

The compounds of the instant invention are also expected to be useful in the treatment of anxiety and of panic as demonstrated by means of standard pharmacological procedures.

Thus, according to a further aspect of the present invention, there is provided the use of a compound selected from formula (I)–(XXV) as a medicament.

As a yet further aspect, there is provided the use of a compound selected from formula (I)–(XXV) in the manufacture of a medicament for the treatment of a disease selected from epilepsy, faintness attacks, hypokinesia, cranial disorders, neurodegenerative disorders, depression, anxiety, panic, pain, irritable bowel syndrome, sleep disorders, osteoarthritis, rheumatoid arthritis, neuropathological disorders, visceral pain, functional bowel disorders, inflammatory bowel diseases, pain associated with dysmenorrhea, pelvic pain, cystitis and pancreatitis.

As a alternative aspect, there is provided a method for treating a disease selected from epilepsy, faintness attacks, hypokinesia, cranial disorders, neurodegenerative disorders, depression, anxiety, panic, pain, irritable bowel syndrome, sleep disorders, osteoarthritis, rheumatoid arthritis, neuropathological disorders, visceral pain, functional bowel disorders, inflammatory bowel diseases, pain associated with dysmenorrhea, pelvic pain, cystitis and pancreatitis comprising administering a therapeutically effective amount of a compound selected from formula (I)–(XXV) to a mammal in need of said treatment.

The biological activity of the compounds of the invention may be measured in a radioligand binding assay using [$^3$H]gabapentin and the $\alpha_2\delta$ subunit derived from porcine brain tissue (Gee N. S., Brown J. P., Dissanayake V. U. K., Offord J., Thurlow R., Woodruff G. N., ADVANCEADVANCE *J. Biol. Chem.*, 1996;271:5879–5776). Results may be expressed in terms of $\mu$M or nM $\alpha 2\delta$ binding affinity.

The compounds of the instant invention may be administered in combination, either separately, simultaneously or sequentially, with one or more other pharmacologically active agents. Suitable agents, particularly for the treatment of pain, include:

(i) opioid analgesics, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine and pentazocine;

(ii) nonsteroidal antiinflammatory drugs (NSAIDs), e.g. aspirin, diclofenac, diflusinal, etodolac, fenbufen, fenoprofen, flufenisal, flurbiprofen,ibuprofen, indomethacin, ketoprofen, ketorolac, meclofenamic acid, mefenamic acid, nabumetone, naproxen, oxaprozin, phenylbutazone, piroxicam, sulindac, tolmetin, zomepirac, and their pharmaceutically acceptable salts;

(iii) barbiturate sedatives, e.g. amobarbital, aprobarbital, butabarbital, butabital, mephobarbital, metharbital, methohexital, pentobarbital, phenobartital, secobarbital, talbutal, theamylal, thiopental and their pharmaceutically acceptable salts;

(iv) benzodiazepines having a sedative action, e.g. chlordiazepoxide, clorazepate, diazepam, flurazepam, lorazepam, oxazepam, temazepam, triazolam and their pharmaceutically acceptable salts, (v) $H_1$ antagonists having a sedative action, e.g. diphenhydramine, pyrilamine, promethazine, chlorpheniramine, chlorcyclizine and their pharmaceutically acceptable salts;

(vi) miscellaneous sedatives such as glutethimide, meprobamate, methaqualone, dichloralphenazone and their pharmaceutically acceptable salts;

(vii) skeletal muscle relaxants, e.g. baclofen, carisoprodol, chlorzoxazone, cyclobenzaprine, methocarbamol, orphrenadine and their pharmaceutically acceptable salts, (viii) NMDA receptor antagonists, e.g. dextromethorphan ((+)-3-hydroxy-N-methylmorphinan) and its metabolite dextrorphan ((+)-3-hydroxy-N-methylmorphinan), ketamine, memantine, pyrroloquinoline quinone and cis-4-(phosphonomethyl)-2-piperidinecarboxylic acid and their pharmaceutically acceptable salts;

(ix) alpha-adrenergic active compounds, e.g. doxazosin, tamsulosin, clonidine and 4-amino-6,7-dimethoxy-2-(5-methanesulfonamido-1,2,3,4-tetrahydroisoquinol-2-yl)-5-(2-pyridyl) quinazoline;

(x) tricyclic antidepressants, e.g. desipramine, imipramine, amytriptiline and nortriptiline;

(xi) anticonvulsants, e.g. carbamazepine, gabapentin, pregabalin and valproate;

(xii) serotonin reuptake inhibitors, e.g. fluoxetine, paroxetine, citalopram and sertraline;

(xiii) mixed serotonin-noradrenaline reuptake inhibitors, e.g. milnacipran, venlafaxine and duloxetine;

(xiv) noradrenaline reuptake inhibitors, e.g. reboxetine;

(xv) Tachykinin (NK) antagonists, particularly Nk-3, NK-2 and NK-1 e.g. antagonists, ($\alpha$R,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthridine-6-13-dione (TAK-637),5-[[(2R,3S)-2-[(1R)-1-[3,5-bis(trifluoromethyl)phenyl]ethoxy-3-(4-fluorophenyl)-4-morpholinyl]methyl]-1,2-dihydro-3H-1,2,4-triazol-3-one (MK-869), lanepitant, dapitant and 3-[[2-methoxy-5-(trifluoromethoxy)phenyl]methylamino]-2-phenyl-piperidine (2S,3S)

(xvi) Muscarinic antagonists, e.g oxybutin, tolterodine, propiverine, tropsium chloride and darifenacin;

(xvii) PDEV inhibitors such as sildenafil, vardenafil and Cialis (Trade Mark);

(xviii) COX-2 inhibitors, e.g. celecoxib, rofecoxib and valdecoxib;

(xix) Non-selective COX inhibitors (preferably with GI protection), e.g. nitroflurbiprofen (HCT-1026);

(xx) coal-tar analgesics, in particular, paracetamol;

(xxi) neuroleptics, such as droperidol;

(xxii) Vanilloid receptor agonists, e.g. resinferatoxin;

(xxiii) Beta-adrenergic compounds such as propranolol;

(xxiv) Local anaesthetics, such as mexiletine;

(xxv) Corticosteriods, such as dexamethasone (xxvi) serotonin receptor agonists and antagonists;

(xxvii) cholinergic (nicotinic) analgesics; and (xxviii) miscellaneous agents such as Tramadol®;

Combinations of the compounds of the present invention and other therapeutic agents may be administered separately, sequentially or simultaneously. Thus, the present invention extends to a kit comprising a compound of formula (I)–(XXV), one or more other therapeutic agents, such as those listed above, and a suitable container.

The compounds of the invention can be administered alone but will generally be administered in an admixture with suitable pharmaceutical excipient(s), diluent(s) or carrier selected with regard to the intended route of administration and standard pharmaceutical practice. If appropriate auxiliaries can be added. Auxiliaries are preservatives, antioxidants, flavours or colourants. The compound of the invention may be of immediate-, delayed-, modified-, sustained-, pulsed- or controlled-release type.

The compounds of invention can be administered, for example but not limited to the following route: orally, buccally or sublingually in the form of tablets, capsules, multi-and nano-particulates, gels, films (incl. mucoadhesive), powder, ovules, elixirs, lozenges (inc. liquid-filled), chews, solutions, suspensions and sprays. The compounds of the invention may also be administered as osmotic dosage form, or in the form of a high energy dispersion or as coated particles or fast-dissolving, fast-disintegrating dosage form as described in Ashley Publications, 2001 by Liang and Chen. The compounds of the invention may be administered as crystalline or amorphous products, freeze dried or spray dried. Suitable formulations of the compounds of the invention may be in hydrophilic or hydrophobic matrix, ion-exchange resin complex, coated or uncoated form and other types as described in U.S. Pat. No. 6,106,864 as desired. Such pharmaceutical compositions, for example, tablets, may contain excipients such as microcrystalline cellulose, lactose, sodium citrate, calcium carbonate, dibasic calcium phosphate, glycine and starch (preferably corn, potato or tapioca starch), mannitol, disintegrants such as sodium starch glycolate, crosscarmellose sodium and certain complex silicates, and granulation binders such as polyvinylpyrrolidone, hydroxypropylmethylcellulose (HPMC), triglycerides, hydroxypropylcellulose (HPC), bentonite sucrose, sorbitol, gelatin and acacia. Additionally, lubricating agents may be added to solid compositions such as magnesium stearate, stearic acid, glyceryl behenate, PEG and talc or wetting agents, such as sodium lauryl sulphate. Additionally, polymers such as carbohydrates, phospoholipids and proteins may be included.

Fast dispersing or dissolving dosage fromulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol or xylitol. The terms dispersing or dissolving as used herein to describe FDDFs are dependent upon the solubility of the drug substance used, i.e. where the drug substance is insoluble a fast dispersing dosage form can be prepared and where the drug substance is soluble a fast dissolving dosage form can be prepared.

The solid dosage form, such as tablets are manufactured by a standard process, for example, direct compression or a wet, dry or melt granulation, melt congealing and extrusion process. The tablet cores which may be mono or multi-layer may be coated with appropriate overcoats known in the art.

Solid compositions of a similar type may also be employed as fillers in capsules such as gelatin, starch or HPMC capsules. Preferred excipients in this regard include lactose, starch, a cellulose, milk sugar or high molecular weight polyethylene glycols. Liquid compositions may be employed as fillers in soft or hard capsules such as gelatin capsule. For aqueous and oily suspensions, solutions, syrups and/or elixirs, the compounds of the invention may be combined with various sweetening or flavouring agents, colouring matter or dyes, with emulsifying and/or suspending agents and with diluents such as water, ethanol, propylene glycol, methylcellulose, alginic acid or sodium alginate, glycerin, oils, hydrocolloid agents and combinations thereof. Moreover, formulations containing these compounds and excipients may be presented as a dry product for constitution with water or other suitable vehicles before use.

Liquid form preparations include solutions, suspensions, and emulsions, for example, water or water propylene glycol solutions. For parenteral injection liquid preparations can be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

The compounds of the present invention can also be administered by injection, that is, intravenously, intramuscularly, intracutaneously, intraduodenally, or intraperitoneally, intraarterially, intrathecally, intraventricularly, intraurethrally, intrastemally, intracranially, intraspinally or subcutaneously, or they may be administered by infusion, needle-free injectors or implant injection techniques. For such parenteral administration they are best used in the form of a sterile aqueous solution, suspension or emulsion (or system so that can include micelles) which may contain other substances known in the art, for example, enough salts or carbohydrates such as glucose to make the solution isotonic with blood. The aqueous solutions should be suitably buffered (preferably to a pH of from 3 to 9), if necessary. For some forms of parenteral administration they may be used in the form of a sterile non-aqueous system such as fixed oils, including mono- or diglycerides, and fatty acids, including oleic acid. The preparation of suitable parenteral formulations under sterile conditions for example lyophilisation is readily accomplished by standard pharmaceutical techniques well-known to those skilled in the art. Alternatively, the active ingredient may be in powder form for constitution with a suitable vehicle (e.g. sterile, pyrogen-free water) before use.

Also, the compounds of the present invention can be administered intranasally or by inhalation. They are conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomiser (preferably an atomiser using electrohydrodynamics to produce a fine mist) or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide, a further perfluorinated hydrocarbon such as Perflubron (trade mark) or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol (optionally, aqueous ethanol) or a suitable agent for dispersing, solubilising or extending release and the propellant as the solvent, which may additionally contain a lubricant, e.g. sorbitan trioleate. Capsules, blisters and cartridges (made, for example, from gelatin or HPMC) for use in an inhaler or insufflator may be formulated to contain a powder mix of the compound of the invention, a suitable powder base such as lactose or starch and a performance modifier such as 1-leucine, mannitol or magnesium stearate.

Prior to use in a dry powder formulation or suspension formulation for inhalation the compound of the invention will be micronised to a size suitable for delivery by inhalation (typically considered as less than 5 microns). Micronisation could be achieved by a range of methods, for example spiral jet milling, fluid bed jet milling, use of supercritical fluid crystallisation or by spray drying.

A suitable solution formulation for use in an atomiser using electrohydrodynamics to produce a fine mist may contain from 1 $\mu$g to 10 mg of the compound of the invention per actuation and the actuation volume may vary from 1 to 100 $\mu$l. A typical formulation may comprise a compound of the invention, propylene glycol, sterile water, ethanol and sodium chloride. Alternative solvents may be used in place of propylene glycol, for example glycerol or polyethylene glycol.

Alternatively, the compounds of the invention may be administered topically to the skin, mucosa, dermally or transdermally, for example, in the form of a gel, hydrogel, lotion, solution, cream, ointment, dusting powder, dressing, foam, film, skin patch, wafers, implant, sponges, fibres, bandage, microemulsions and combinations thereof For such applications, the compounds of the invention can be suspended or dissolved in, for example, a mixture with one or more of the following: mineral oil, liquid petrolatum, white petrolatum, propylene glycol, polyoxyethylene polyoxypropylene compound, emulsifying wax , fixed oils, including synthetic mono- or diglycerides, and fatty acids, including oleic acid, water, sorbitan monostearate, a polyethylene glycol, liquid paraffin, polysorbate 60, cetyl esters wax, cetearyl alcohol, 2-octyldodecanol, benzyl alcohol, alcohols such as ethanol. Alternatively, penetration enhancers may be used. The following may also be used polymers, carbohydrates, proteins, phospolipids in the form of nanoparticles (such as niosomes or liposomes) or suspended or dissolved. In addition, they may be delivered using iontophoresis, electroporation, phonophoresis and sonophoresis.

Alternatively, the compounds of the invention can be administered rectally, for example in the form of a suppository or pessary. They may also be administered by vaginal route. For example, these compositions may be prepared by mixing the drug with a suitable non-irritant excipients, such as cocoa butter, synthetic glyceride esters or polyethylene glycols, which are solid at ordinary temperatures, but liquefy and/or dissolve in the cavity to release the drug.

The compounds of the invention may also be administered by the ocular route. For ophthalmic use, the compounds can be formulated as micronised suspensions in isotonic, pH adjusted, sterile saline, or, preferably, as solutions in isotonic, pH adjusted, sterile saline. A polymer may be added such as crossed-linked polyacrylic acid, polyvinylalcohol, hyaluronic acid, a cellulosic polymer (e.g. hydroxypropylmethylcellulose, hydroxyethylcellulose, methyl cellulose), or a heteropolysaccharide polymer (e.g. gelan gum). Alternatively, they may be formulated in an ointment such as petrolatum or mineral oil, incorporated into bio-degradable (e.g. absorbable gel sponges, collagen) or non-biodegradable (e.g. silicone) implants, wafers, drops, lenses or delivered via particulate or vesicular systems such as niosomes or liposomes. Formulations may be optionally combined with a preservative, such as benzalkonium chloride. In addition, they may be delivered using iontophoresis. They may also be administered in the ear, using for example but not limited to the drops.

The compounds of the invention may also be used in combination with a cyclodextrin. Cyclodextrins are known to form inclusion and non-inclusion complexes with drug molecules. Formation of a drug-cyclodextrin complex may modify the solubility, dissolution rate, taste-masking, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

The term 'administered' includes delivery by viral or non-viral techniques. Viral delivery mechanisms include but are not limited to adenoviral vectors, adeno-associated viral (AAV) vectors, herpes viral vectors, retroviral vectors, lentiviral vectors, and baculoviral vectors. Non-viral delivery mechanisms include lipid mediated transfection, lipsomes, immunoliposomes, lipofectin, cationic facial amphiphiles (CFAs) and combinations thereof. The routes for such delivery mechanisms include but are not limited to mucosal, nasal, oral, parenteral, gastrointestinal, topical or sublingual routes.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form. The quantity of active component in a unit dose preparation may be varied or adjusted from 0.1 mg to 1 g according to the particular application and the potency of the active component. In medical use the drug may be administered three times daily as, for example, capsules of 100 or 300 mg. In therapeutic use, the compounds utilized in the pharmaceutical method of this invention are administered at the initial dosage of about 0.01 mg to about 100 mg/kg daily. A daily dose range of about 0.01 mg to about 100 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The pharmaceutical composition according to the present invention can, if desired, also contain one or more other compatible therapeutic agents. In particular, the composition can be combined with any one or more compounds useful in the treatment of pain, such as those listed above. Thus, the present invention presents a pharmaceutical composition comprising a compound selected from formula (I)–(XXV), one or more other pharmacologically active agents and one or more pharmaceutically acceptable carriers.

General Methods

The above compounds can be synthesised from the ketones (1)–(12) below, in which $R^1$ and $R^2$ have the same meanings as give above:

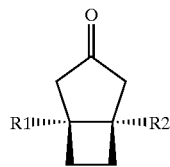

(1)

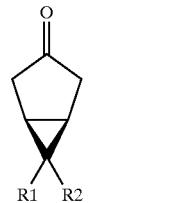

(2)

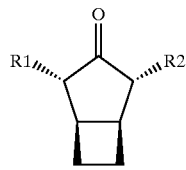

(3)

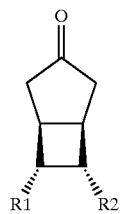

(4)

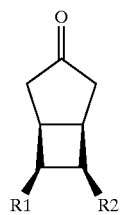

(5)

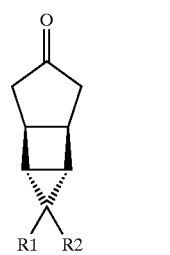

(6)

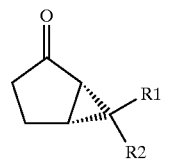

(7)

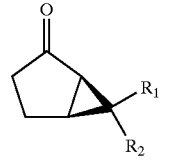

8(6)

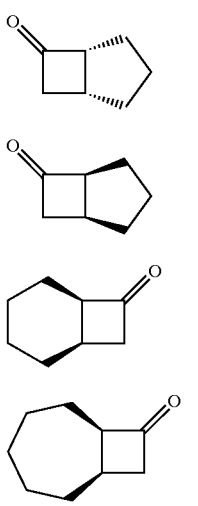

(9)

(10)

(11)

(12)

Intermediates of formulae (1) to (6) above are believed to be novel and constitute a further aspect of the present invention. Particularly suitable intermediate ketones according to the present invention are selected from:

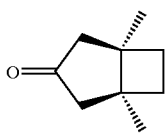

(1a)

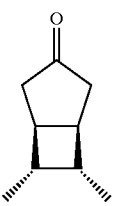

(4a)

and

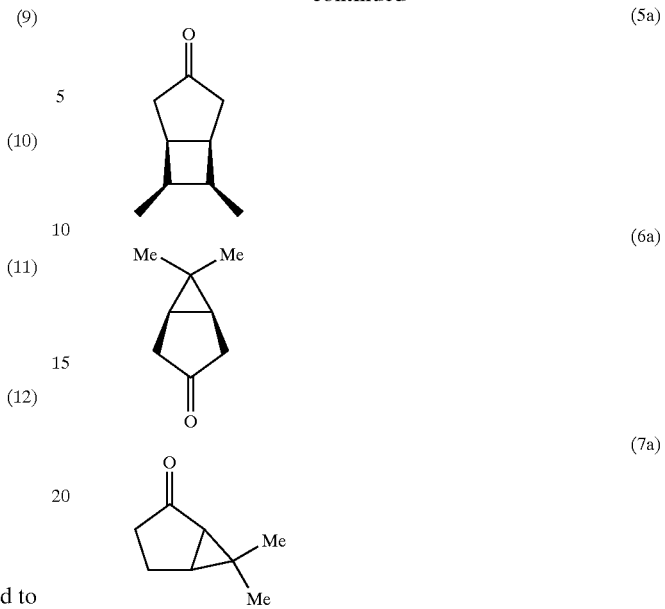

(5a)

(6a)

(7a)

Various methods for synthesizing the above ketones are set out below:

A. Syntheses of Ketones 1–12

(1) Synthesis of Ketones of Type (1)

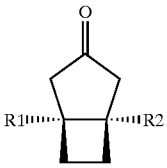

1

For Example:

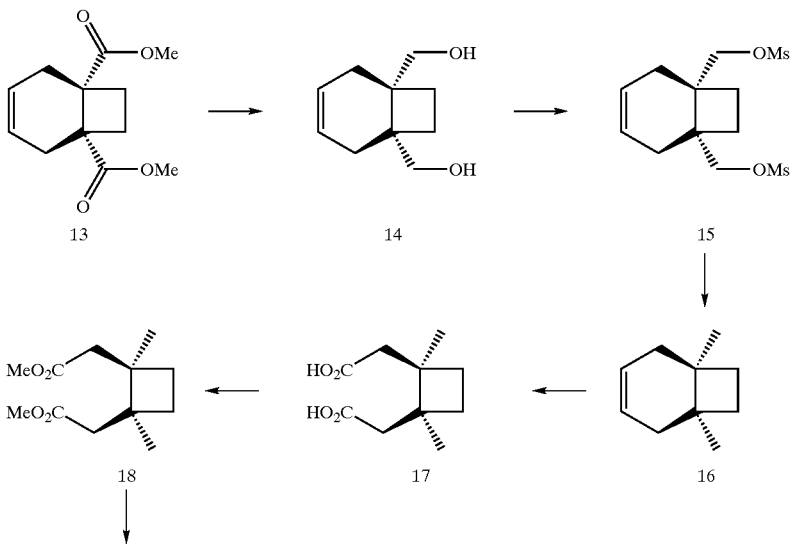

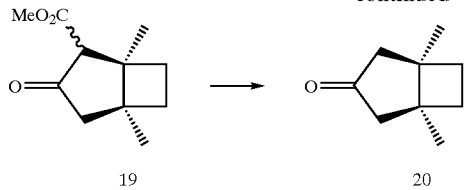

(a) The known diester (13) is reduced to diol (14) e.g. by lithium aluminium hydride in an organic solvent e.g. tetrahydrofuran or diethyl ether at a temperature of 0° C. to reflux.
(b) The diol (14) is added to methylsulfonyl chloride in pyridine or triethylamine in dichloromethane a −60° C. to 40° C. to produce a dimesylate of formula (15).
(c) The dimesylate (15) is added to a solution of lithium aluminium hydride in a solvent such as tetrahydrofuran or diethyl ether at a temperature of from 0° C. to reflux to produce an alkene of formula (16).
(d) The alkene (16) above is added
 to a mixture of carbon tetrachloride or ethyl acetate and acetonitrile to which water, sodium periodate and ruthenium (III) chloride were added, and stirred at a temperature from −40° C. to 80° C. to produce carboxylic acid of formula (17); or
 to a mixture of potassium permanganate in water and dichloromethane in the presence of a phase transfer catalyst such as tetrabutylammonium bromide to produce (17).
(e) The carboxylic acid (17) is added to a mixture of an alcohol such as methanol and a concentrated acid such as sulphuric acid or hydrochloric acid at a temperature of room temperature to reflux to produce diester of formula (18).
(f) The diester (18) above is added to a strong base such as sodium hydride or potassium tert-butoxide in a solvent such as tetrahydrofuran at reflux temperature to give ketone (19).
(g) The ketone (19) above is added to a mixture of dimethyl sulphoxide and water at a temperature of 100–180° C. to produce ketone of formula (20).

(2) Synthesis of Ketones of Type (4) and (5)

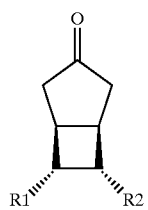

4

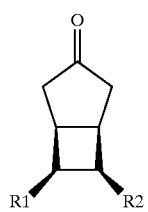

5

For Example:

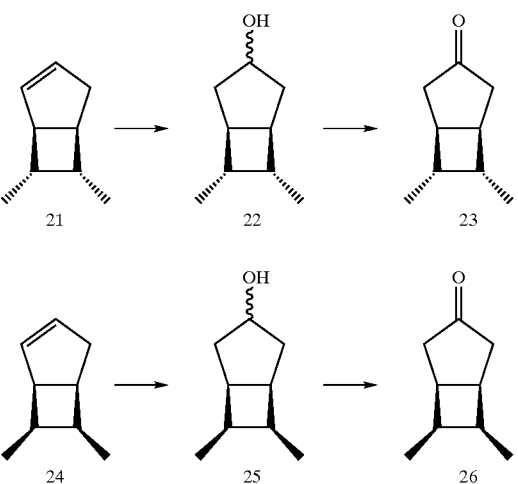

(a) The known alkene (21), see B. D. Kramer, P. D. Bartlett, *J. Am. Chem. Soc.*, 1972, 94, 3934, is mixed with an organoborane such as disiamylborane, thexylborane or 9-BBN in a solvent such as diethyl ether or tetrahydrofuran at a temperature of 0° C. to room temperature. The resulting organoborane is mixed with a solution of concentrated sodium hydroxide and hydrogen peroxide to give an alcohol of formula (22).
(b) The alcohol (22) is oxidized, e.g. with an oxidising agent such as chromium trioxide, pyridinium dichromate or pyridinium chlorochromate in a solvent such as dichloromethane or acetone to give the ketone of formula (23).

A similar process can be used for ketone (25) except that the starting material is the known alkene (24), see B. D. Kramer, P. D. Bartlett, supra.

(3). Synthesis of Ketones of Type (3)

3

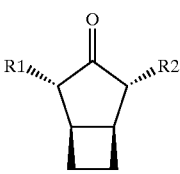

For Example:

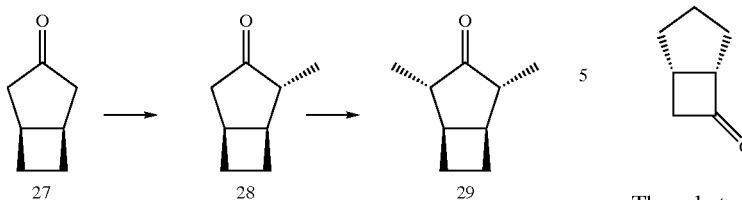

(a) The known ketone (27) see U.S. No. 60/160725, is added to a strong base such as lithium diisopropylamide or lithium hexamethyldisilazide followed by a methylating agent such as methyl iodide in a solvent such as tetrahydrofuran or diethyl ether at a temperature of between −100° C. and room temperature to give the ketone of formula (28).

(b) The ketone of formula (46) above is further methylated with a methylating agent such as methyl iodide in the presence of a strong base such as lithium diisopropylamide or lithium hexamethyldisilazide in a solvent such as tetrahydrofuran or diethyl ether at a temperature of between −100° C. and room temperature to give the product ketone of formula (29).

(4). Synthesis of Ketones of Type (9) and (10)

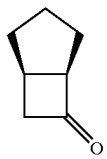

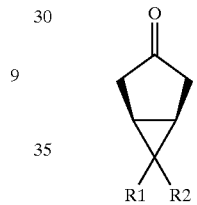

These ketones are known compounds, see L. Y. Chen, L. Ghosez, *Tetrahedron Letters,* 1990, 31, 4467; C. Houge, A. M. Frisque-Hesbain, A. Mockel, L. Ghosez, J. P. Declercq, G. Germain, M. Van Meerssche, J. Am. Chem. Soc., 1982, 104, 2920.

These ketones may also be prepared from the known unsaturated ketone of general formula (76)

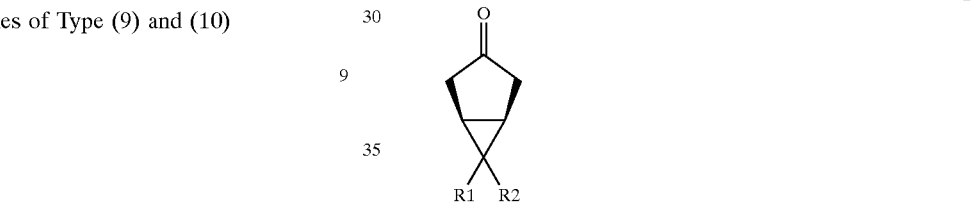

by reduction by hydrogenation with a suitable catalyst such as Pd/C in a suitable solvent such as ethyl acetate.

(5). Synthesis of Ketones of Type (2)

For Example:

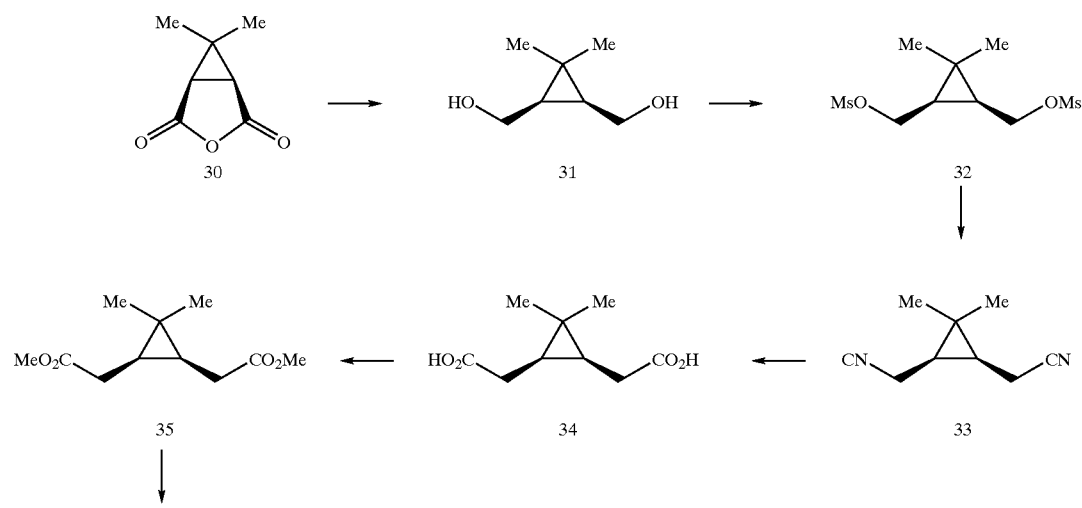

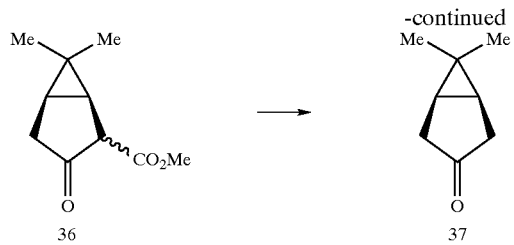

(a) The known carbamate (30), see W. Von der Saal, R. Reinhardt, H. M. Seidenspinner, J. Stawitz, H. Quast, *Liebigs Ann. Chem.*, 1989, 703; Z. Cekovic, R. Matovic, *J. Serb. Chem. Soc.*, 1988, 53, 595, is reduced using lithium aluminium hydride in a solvent such as tetrahydrofuran or diethyl ether at a temperature of 0° C. to reflux to give diol (31).

(b) The diol (31) is added to methylsulphonyl chloride in pyridine or triethylamine in dichloromethane at a temperature of −60° C. to 40° C. to produce dimesylate of formula (32).

(c) The dimesylate (32) is added to sodium or potassium cyanide in a solvent such as tetrahydrofuran, diethyl ether, dimethylsulphoxide or dimethylformamide at a temperature of 0° C. to reflux to give the dicyanide of structure (33).

(d) The dicyanide (33) is added to a concentrated solution of potassium or sodium hydroxide at a temperature of 50° C. to reflux to give diacid (34).

(e) The diacid (34) is esterified to diester (35) by addition:
  to a mixture of iodomethane in a solvent selected from dichloromethane, chloroform, tetrahydrofuran, toluene or 1,4-dioxane to which a base such as 1,8-diazabicyclo[5.4.0]undec-7-ene (DBU), triethylamine or 1,5-diazabicyclo[4.3.0]non-5-ene (DBN) is added and stirred at a temperature from −40° C. to 100° C.; or
  to a mixture of methanol and a concentrated acid such as sulphuric acid or hydrochloric acid at a temperature ranging from 0° C. to 100° C.; or
  to trimethylsilyldiazomethane and methanol in benzene or toluene at a temperature from −40° C. to 100° C.; or
  to diazomethane in a solvent such as benzene, toluene, dichloromethane at a temperature from −40° C. to 40° C.

(f) The diester (35) is added to a strong base such as sodium hydride or potassium tert-butoxide in a solvent such as tetrahydrofuran at reflux temperature to give ketone (36).

(g) The ketone (36) above is added to a mixture of dimethyl sulphoxide and water at a temperature of 100–180° C. to produce ketone of formula (37).

(6). Synthesis of ketones of type 7 and 8

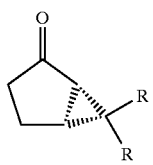

7

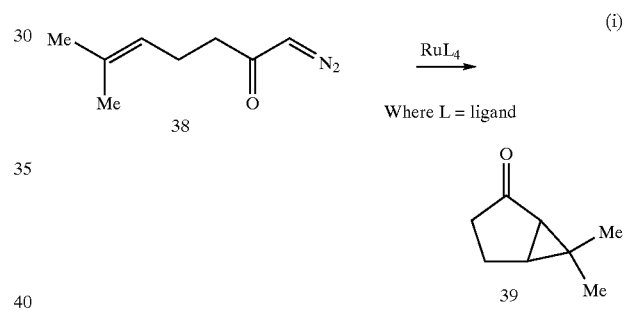

Ketones of this type can be made using ruthenium complexes, see S-W. Park, J-H. Son, S-G. Kim, K. H. Ahn, *Tetrahedron: Asymmetry*, 1999, 10, 1903.

For Example:

The known alkene (38), see H. Nishiyama, Y. Itoh, H. Matsumoto, S. B. Park, K. Itoh, *J. Am. Chem. Soc.*, 1994, 116, 2223, was stirred with a ruthenium catalyst such as $Cl_2Ru(pybox\text{-}ip)(CH_2=CH_2)$ in a solvent such as dichloromethane or chloroform at a temperature of 0° C. to room temperature to give ketone of structure (39).

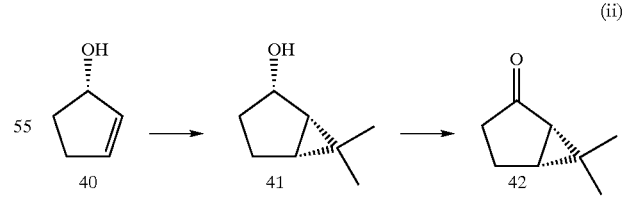

(a) The known alcohol (40), see M. Asami, *Bull. Chem. Soc. Jpn.*, 1990, 63, 721; T. Sato, Y. Gotoh, Y. Wakabayashi, T. Fujisawa, *Tetrahedron Letters*, 1983, 24, 4123, is mixed with diiodomethane and an alkylzinc such as dimethylzinc or diethylzinc or a zinc-copper couple in a solvent such as toluene or benzene at a temperature of −60° C. to reflux to give an alcohol of formula (41).

(b) The alcohol of formula (41) is added to an oxidising agent such as chromium trioxide, pyridinium dichromate or pyridinium chlorochromate in a solvent such as dichloromethane or acetone to give the ketone of formula (42).

(7). Synthesis of Ketones of Type (6)

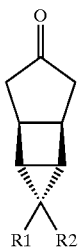

For Example:

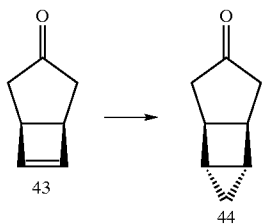

The known ketone (43), see W. A. Wilczak, D. I. Schuster, *Tetrahedron Letters,* 1986, 27, 5331; D. I. Schuster, J. Eriksen, J. Org. Chem, 1979, 44, 4254, is mixed with diiodomethane and an alkylzinc such as dimethylzinc or diethylzinc or a zinc-copper couple in a solvent such as toluene or benzene at a temperature of −60° C. to reflux to give ketone of structure (44).

(8). Synthesis of Ketones of Type (11) and (12)

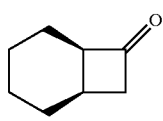

(11)

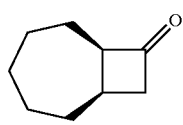

(12)

Preparation of (11) can be found in the following references:

Ogino, Toshio. Preparation of bicyclo[4.2.0]octan-7-ones. Niigata Daigaku Kyoikugakubu Kiyo, Shizen Kagaku Hen (1973), 15 26–33.

Marko, Istvan; Ronsmans, Bruno; Hesbain-Frisque, Anne Marie; Dumas, Stephane; Ghosez, Leon; Ernst, Beat; Greuter, Hans. Intramolecular [2+2] cycloadditions of ketenes and keteniminium salts to olefins. J. Am. Chem. Soc. (1985), 107(7), 2192–4.

Chen, Lian Yong; Ghosez, Leon. Study of chiral auxiliaries for the intramolecular [2+2] cycloaddition of a keteniminium salt to an olefinic double bond. A new asymmetric synthesis of cyclobutanones. Tetrahedron Lett. (1990), 31(31), 4467–70.

Preparation of (12) can be found in Marko et al., supra.

B. Conversion of Ketone Starting Materials into Amino Acids of the Invention

The above ketones can be transformed into amino acids using one of the following general methods A to E, as illustrated below for ketone (1) where $R^1=R^2$=methyl.

Method A:

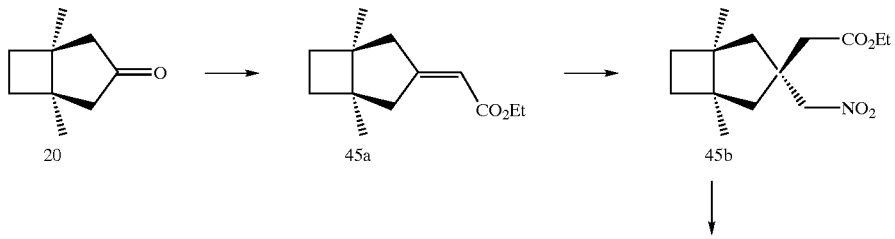

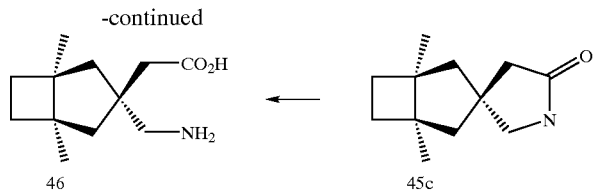

(a) The ketone (20) is converted to unsaturated ester (45a) by reaction with with a trialkylphosphonoacetate such as triethylphosphonoacetate in the presence of a base. Suitable bases include sodium hydride, potassium hydride, lithium- or sodium- or potassium-hexamethyldisilazide, butyllithium or potassium tert-butoxide. The reaction may be carried out in a polar aprotic organic solvent such as tetrahydrofuran, dimethylformamide, diethyl ether or dimethylsulfoxide at a temperature in the range from −78° C. to 100° C.

(b) Nitromethane is added to the unsaturated ester (45a) by a Michael addition reaction in the presence of a base and in a polar aprotic organic solvent at a temperature of −20° C. to 100° C. to give the nitroester (45b). Suitable bases include tetrabutylammonium fluoride, tetramethylguanidine, 1,5-diaza-bicyclo[4,3,0]non-5-ene, 1,8-diazabicyclo[5,4,0]undec-7-ene, a sodium or potassium alkoxide such as potassium tert-butoxide, potassium carbonate, sodium hydride or potassium fluoride. Suitable organic solvents include tetrahydrofuran, diethyl ether, dimethylfornamide, dimethylsulphoxide, benzene, toluene, dichloromethane, chloroform or tetrachloromethane.

(c) Reduction of the nitro ester (45b) and ring closure by reaction of the resulting amino group with the ester group gives the cyclic lactam (45c). Hydrogenation may be in the presence of a catalyst such as Raney nickel, palladium on charcoal or rhodium catalyst or other nickel or palladium containing catalyst in a solvent such as methanol, ethanol, isopropanol, ethyl acetate, acetic acid, 1,4-dioxane, chloroform or diethyl ether at a temperature in the range from 20° C. to 80° C.

(d) Hydrolysis of the cyclic lactam (45c) e.g. using aqueous hydrochloric acid at a concentration of from 0.01 M to 12 M and optionally in the presence of a solvent such as 1,4-dioxane, acetic acid or water produces the amino acid (46).

Method B:

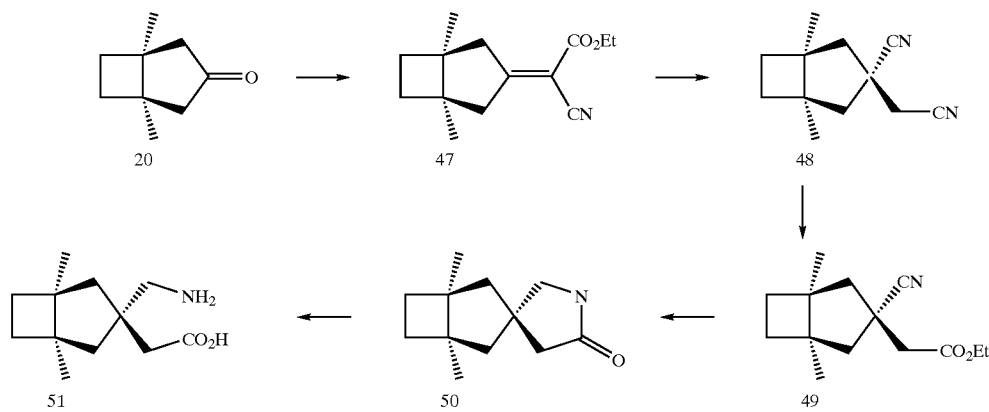

(a) The ketone (20) is condensed with an alkyl cyanoacetate, for example ethyl cyanoacetate in an organic solvent selected from toluene, benzene, xylenes or n-heptane to which acetic acid and β-alanine or ammonium acetate, or piperidine are added. The mixture is stirred at a temperature from 0° C. to 150° C. with removal of water by, for example, use of a Dean-Stark trap or activated molecular sieves, to produce the cyanoester of formula (47).

(b) The cyanoester (47) is converted to dicyanide (48) by treatment with potassium cyanide or sodium cyanide in water and ethanol or methanol. The mixture is refluxed and water is removed by, for example, use of a Dean-Stark trap.

(c) The cyanomethyl group of dicyanide (48) converted to an ethoxycarbonylmethyl group by reaction with ethanol in toluene or benzene saturated with gaseous hydrochloric acid. The reaction temperature may be from −30° C. to 40° C.

(d) The cyano-group of the resulting cyanoester (49) is reduced by hydrogenation in methanol, ethanol or ethyl acetate using a catalyst such as nickel, palladium, platinum or rhodium at a temperature from 15° C. to 60° C., after which ring closure gives lactam (50).

(e) Hydrolysis of the lactam (50) e.g. using aqueous hydrochloric acid at a concentration of from 0.01 M to 12 M and optionally in the presence of a solvent such as 1,4-dioxane, acetic acid or water produce the amino acid (51).

Method C:

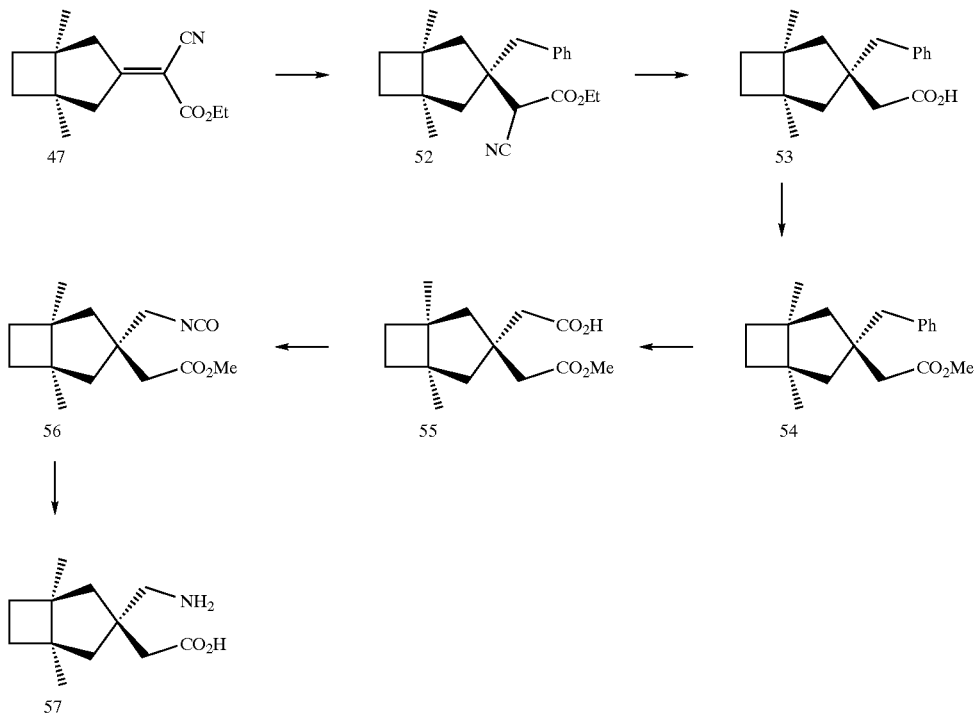

(a) Cyanoester (47) is added to a mixture of benzylmagnesium chloride, bromide or iodide, in a dry solvent e.g. tetrahydrofuran, 1,4-dioxane, n-heptane, toluene, diethyl ether, or tert-butyl methyl ether at a temperature from −100° C. to 110° C. resulting in cyanoester of formula (52).

(b) The cyano group of cyanoester (52) is removed by means of a base e.g. potassium hydroxide, sodium hydroxide, lithium hydroxide or cesium hydroxide in a solvent e.g. ethylene glycol, 2-methoxyethyl ether, 1,4-dioxane or diethylene glycol. The mixture is stirred at a temperature from 25° C. to 250° C. to produce the carboxylic acid of formula (53).

(c) The carboxylic acid group of acid (53) is protected by conversion to its alkyl of 1–6 carbon atoms ester, e.g. its methyl ester (54). For this purpose, acid (53) may be added
   to a mixture of iodomethane in a solvent selected from dichloromethane, chloroform, tetrahydrofuran, toluene or 1,4-dioxane to which a base such as 1,8-diazabicyclo[5.4.0]undec-7-ene (DBU), triethylamine or 1,5-diazabicyclo[4.3.0]non-5-ene (DBN) is added and stirred at a temperature from −40° C. to 110° C.; or
   to a mixture of methanol and a concentrated acid such as sulphuric acid or hydrochloric acid at a temperature ranging from 0° C. to 100° C.; or
   to trimethylsilyldiazomethane and methanol in benzene or toluene at a temperature from −40° C. to 100° C.; or
   to diazomethane in a solvent such as benzene, toluene, dichloromethane at a temperature from −40° C. to 40° C.

(d) The phenyl group of the resulting ester (54) is oxidized to a carboxylic acid group by treatment with sodium periodate and ruthenium (III) chloride in a mixture of carbon tetrachloride or ethyl acetate and acetonitrile to which water is added. The mixture is stirred at a temperature from −40° C. to 80° C. to give carboxylic acid (55).

(e) The carboxylic acid group of acid (55) is converted to isocyanate by addition
   to a mixture of a base selected from triethylamine or diisopropylethylamine and a solvent selected from toluene, benzene, xylenes, tetrahydrofuran, diethyl ether or n-heptane to which diphenylphosphoryl azide (DPPA) is added and stirring at a temperature from 0° C. to 150° C. to produce the isocyanate of formula (26); or
   to ethyl chloroformate or isobutyl chloroformate and a base such as triethylamine or diisopropylethylamine in tetrahydrofuran or acetone or diethyl ether at a temperature of −40° C. to 78° C. followed by addition of sodium azide in water and tetrahydrofuran or acetone followed by addition of toluene or benzene and refluxing.

(f) The isocyanate and ester groups of compound (56) are simultaneously hydrolysed to amino and carboxylic acid groups, e.g. by aqueous hydrochloric acid at a concentration of from 0.01 M to 12 M optionally in the presence of a solvent such as 1,4-dioxane, acetic acid or water to produce the amino acid (57).

Method D:

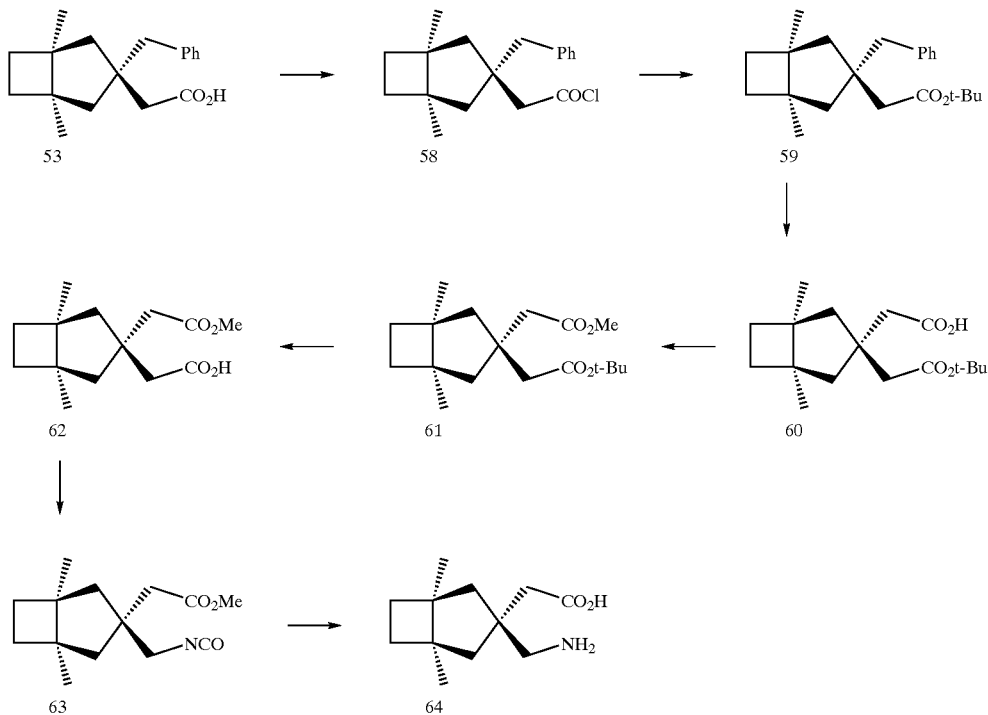

(a) As a first stage in protecting the carboxylic acid group of acid (53), it is converted to its chloride (58) by reaction at a temperature of from −40° C. to 110° C. with e.g. oxalyl chloride or thionyl chloride in an aprotic organic solvent e.g dichloromethane, chloroform, diethyl ether, toluene or tert-butyl methyl ether to which 0.01 mol percent to 10 mol percent of N,N-dimethylformamide (DMF) is added.

(b) The chloride (58) is converted to its tert-butyl ester, e.g. by reaction with tert-butyl alcohol in an aprotic organic solvent e.g. dichloromethane, chloroform, diethyl ether, toluene, or tert-butyl methyl ether to which N,N-diisopropylethylamine (DIPEA) or triethylamine is added. The reaction mixture is stirred at a temperature from −40° C. to 110° C. to produce the ester of formula (59).

(c) The phenyl group of ester (59) is oxidized to a carboxylic acid group by reaction with, sodium periodate and ruthenium (III) chloride in a mixture of carbon tetrachloride or ethyl acetate and acetonitrile to which water is added. The reaction mixture is stirred at a temperature from −40° C. to 80° C. to produce carboxylic acid of formula (60).

(d) The carboxyl group of acid (60) is converted to an ester group by addition to a mixture of iodomethane in a solvent selected from dichloromethane, chloroform, tetrahydrofuran, toluene or 1,4-dioxane to which a base such as 1,8-diazabicyclo[5.4.0]undec-7-ene (DBU), triethylamine or 1,5-diazabicyclo[4.3.0]non-5-ene (DBN) is added and stirred at a temperature from −40° C. to 110° C. to produce the ester of formula (61); or to a mixture of methanol and a concentrated acid such as sulphuric acid or hydrochloric acid at a temperature ranging from 0° C. to 100° C.; or to trimethylsilyldiazomethane and methanol in benzene or toluene at a temperature from −40° C. to 100° C.; or to diazomethane in a solvent such as benzene, toluene, dichloromethane at a temperature from −40° C. to 40° C.

(e) The tert-butoxy group is removed from diester (61) by reaction with trifluoroacetic acid in a solvent e.g. dichloromethane, chloroform, 1,4-dioxane, tetrahydrofuran, diethyl ether, or tert-butyl methyl ether. The reaction mixture is stirred from a temperature from −40° C. to 110° C. to give carboxylic acid of formula (62).

(f) The ester group of acid (62) is converted to isocyanate (63) by addition to a mixture of a base selected from triethylamine or diisopropylethylamine and a solvent selected from toluene, benzene, xylenes, tetrahydrofuran, diethyl ether or n-heptane to which diphenylphosphoryl azide (DPPA) is added and stirring at a temperature from 0° C. to 150° C.; or to ethyl chloroformate or isobutyl chloroformate and a base such as triethylamine or diisopropylethylamine in tetrahydrofuran or acetone or diethyl ether at a temperature of −40° C. to 78° C. followed by addition of sodium azide in water and tetrahydrofuran or acetone followed by addition of toluene or benzene and refluxing.

(g) Simultaneous hydrolysis of the isocyanate and ester groups of compound (63) e.g. by aqueous hydrochloric acid at a concentration of from 0.01 M to 12 M in the presence or absence of a solvent such as 1,4-dioxane, acetic acid or water gives the amino acid (64).

Method E:

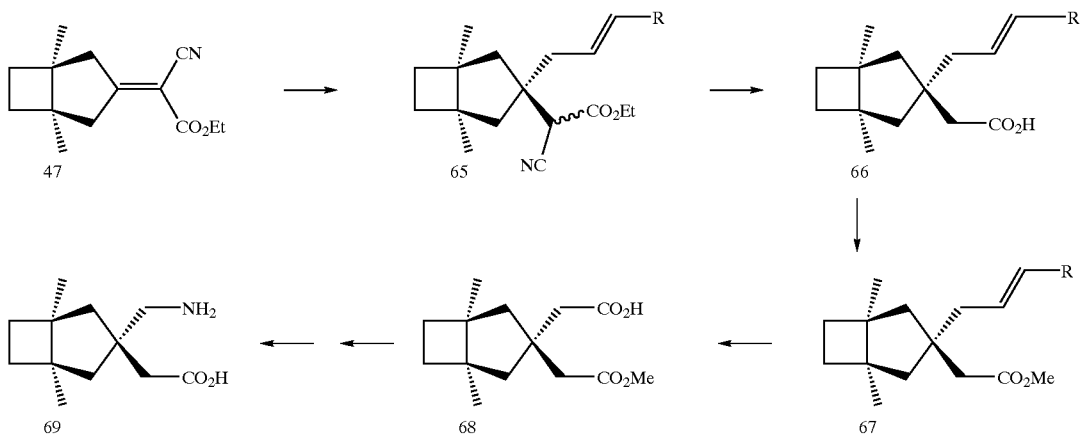

(a) Cyanoester (47) is reacted with allylmagnesium chloride or bromide or 2-butenylmagnesium chloride and a dialkylzinc such as dimethylzinc or a copper (I) salt such as copper (I) iodide or copper (I) cyanide in a dry organic solvent e.g. tetrahydrofuran, 1,4-dioxane, n-heptane, toluene, diethyl ether or tert-butyl methyl ether at a temperature from −100° C. to 110° C. to give an unsaturated addition product of formula (65).

(b) The cyano group of addition product (65) is removed by reaction with a base, e.g. potassium hydroxide, sodium hydroxide, lithium hydroxide or cesium hydroxide in an organic solvent selected from ethylene glycol, 2-methoxyethyl ether, 1,4-dioxane or diethylene glycol. The reaction mixture is stirred at a temperature from 25° C. to 250° C. to give a carboxylic acid of formula (66).

(c) The carboxylic acid group of acid (66) is converted to an ester group by addition

- to a mixture of iodomethane in a solvent selected from dichloromethane, chloroform, tetrahydrofuran, toluene or 1,4-dioxane to which a base such as 1,8-diazabicyclo[5.4.0]undec-7-ene (DBU), triethylamine or 1,5-diazabicyclo[4.3.0]non-5-ene (DBN) was added and stirred at a temperature from −40° C. to 110° C. to produce the ester of formula (67); or

- to a mixture of methanol and a concentrated acid such as sulphuric acid or hydrochloric acid at a temperature ranging from 0° C. to 100° C.; or

- to trimethylsilyldiazomethane and methanol in benzene or toluene at a temperature from −40° C. to 100° C.; or

- to diazomethane in a solvent such as benzene, toluene, dichloromethane at a temperature from −40° C. to 40° C.

(d) The unsaturated group in ester (67) is oxidized by sodium periodate and ruthenium (III) chloride in a mixture of carbon tetrachloride or ethyl acetate and acetonitrile to which water is added. The mixture is stirred at a temperature from −40° C. to 80° C. to give a carboxylic acid of formula (68).

(e) Carboxylic acid (68) is converted to amino acid (69) as in method C.

The above ketones can also be transformed into amino acids using one of the following general methods F to G, as illustrated below for ketone of type (9).

Method F

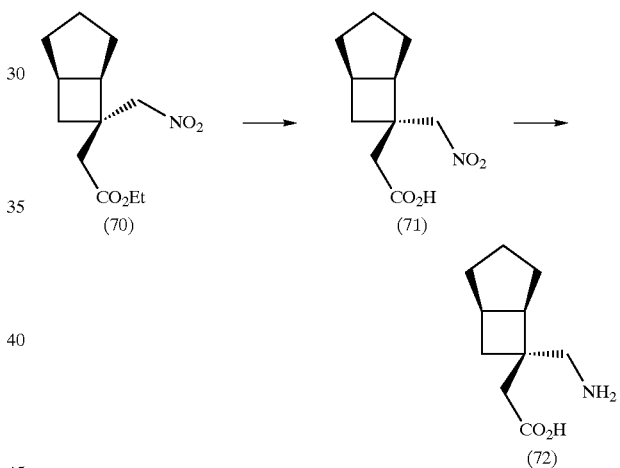

(a) The ketone is converted to the nitro ester (70) according to the methods described hereinabove.

(b) Nitro ester (70) is hydrolysed with a suitable base, such as aqueous sodium hydroxide to give nitro acid (71) which is reduced by suitable hydrogenation, e.g. $H_2$ on a palladium/carbon catalyst in a suitable solvent, such as ethanol to give the amino acid (72).

Method G

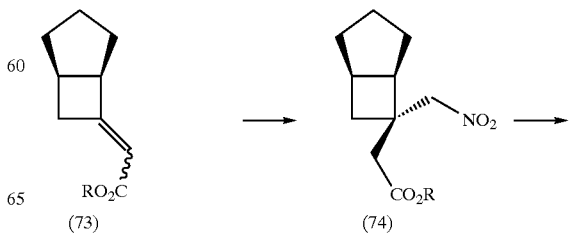

Method I

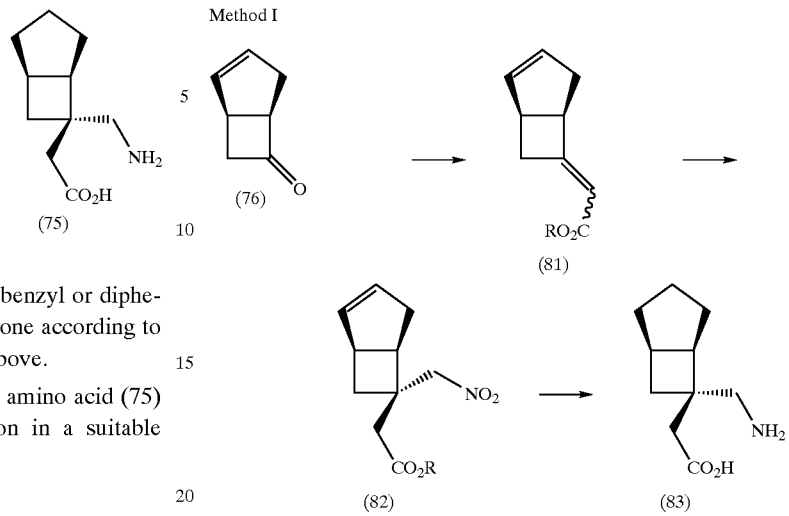

(75)

(a) The unsaturated ester (73), where R is benzyl or diphenylmethyl may be prepared from the ketone according to any of the general methods described above.

(b) The nitro ester (74) is converted to the amino acid (75) by reduction by catalytic hydrogenation in a suitable solvent.

Compounds of the invention may alternatively be prepared from the known unsaturated version of a ketone of type (8) as follows in Methods H and I:

Method H

(76) → (77) → (78) → (79) → (80)

(a) Ketone (76) is converted to the unsaturated nitro ester (78) according to the general methods described hereinabove.

(b) Nitro ester (78) is hydrolysed with a suitable base, such as aqueous sodium hydroxide to give nitro acid (79) which is reduced by hydrogenation, e.g. $H_2$ on a palladium/carbon catalyst in a suitable solvent, such as ethanol to give the amino acid (80).

(a) The unsaturated nitro ester (82) may be prepared from the ketone (76) according to the methods generally described hereinabove.

(b) The nitro ester (82) is converted to the amino acid (83) by reduction by catalytic hydrogenation in a suitable solvent.

A pharmaceutically acceptable salt of a compound of the invention may be readily prepared by mixing together solutions of a compound of the invention and the desired acid or base, as appropriate. The salt may precipitate from solution and be collected by filtration or may be recovered by evaporation of the solvent.

Referring to the general methods above, it will be readily understood to the skilled person that where protecting groups are present, these will be generally interchangeable with other protecting groups of a similar nature, e.g. where an acid group is described as being protected with an ethyl group, this may be readily interchanged with any suitable alkyl group, suitably a $C_{1-6}$alkyl group.

It will be readily understood to the skilled person that particular steps in the general methods presented herein above may be suitably combined in any other manner not shown to provide a compound according to the present invention.

Thus, in summary, the invention provides:

(i) a compound of the formula I-XXV or a pharmaceutically acceptable salt, solvate, polymorph or pro-drug thereof;

(ii) a process for the preparation of a compound of the formula I-XXV or a pharmaceutically acceptable salt, solvate, polymorph or pro-drug thereof;

(iii) a pharmaceutical composition including a compound of the formula I-XXV or a pharmaceutically acceptable salt, solvate, polymorph or pro-drug thereof, together with a pharmaceutically acceptable excipient, diluent or carrier;

(iv) a compound of the formula I-XXV or a pharmaceutically acceptable salt, solvate, polymorph, pro-drug or composition thereof, for use as a medicament;

(v) the use of a compound of the formula I-XXV or of a pharmaceutically acceptable salt, solvate, polymorph, pro-drug or composition thereof, for the manufacture of a medicament for the treatment of any of the conditions mentioned herinbefore;

(vi) the use of a compound of the formula I-XXV or of a pharmaceutically acceptable salt, solvate, polymorph, pro-drug or composition thereof, for the manufacture of a medicament for the treatment of any of the conditions mentioned herinbefore;
(vii) a method of treatment of a mammal to treat any of the conditions mentioned herinbefore, including treating said mammal with an effective amount of a compound of the formula I-XXV or with a pharmaceutically acceptable salt, solvate, polymorph, pro-drug or composition thereof;
(viii) a novel intermediate of the formula (1a), (4a)–(7a), (70), (71), (73), (74), (77)–(79), (81) or (82);
(ix) a method for the treatment of any of the conditions mentioned herinbefore, which comprises administering to a patient in need of such treatment, either simultaneously, separately or sequentially, a combination of a compound of formula I-XXV and a further pain agent.
(x) the use of a combination of a compound of formula I-XXV and a further therapeutic agent for the manufacture of a medicament for the treatment of any of the conditions mentioned herinbefore; and
(xi) a product containing a compound of formula I-XXV and a further therapeutic agent as a combined preparation for simultaneous, separate or sequential use in the treatment of any of the conditions mentioned herinbefore.

The present invention is illustrated by the following non-limiting examples and intermediates.

EXAMPLE 1

[(1R,5R,6S)-6-(Aminomethyl)bicyclo[3.2.0]hept-6-yl]acetic acid hydrochloride

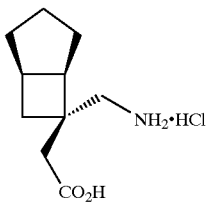

The isocyanate of preparation 9 (approx 9.33 mmol) and 6N hydrochloric acid (30 ml) were refluxed for 18 h. The mixture was allowed to cool, diluted with water (60 ml) and extracted with dichloromethane (2×50 ml). The aqueous phase was concentrated under reduced pressure to give a yellow solid which was washed with ethyl acetate and acetonitrile to give 0.92 g of the title compound as a white solid.

$^1$H-NMR (400 MHz, $d_6$-DMSO): δ=7.94 (3H, br s), 3.15 (1H, d), 3.07 (1H, d), 2.72 (1H, quin), 2.46 (1H, m), 2.42 (1H, d), 2.33 (1H, d), 1.98 (1H, m), 1.80–1.64 (2H, m), 1.59 (1H, m), 1.48–1.28 (3H, m), 1.23 (1H, dd).

LRMS (APCI): m/z [(MH−HCl)$^+$] 184.

LCMS (Prodigy ODS3 (3μ) 150 mm×4.6 mmid column, 20–100% Acetonitrile+0.1% formic acid) Retention Time= 4.34 min, 100% purity.

[α]$_D$(c=0.127 in methanol)=−12.4°

Microanalysis: Found: C, 54.64; H, 8.19; N, 6.42. $C_{10}H_{17}NO_2 \cdot HCl$ requires C, 54.67; H, 8.26; N, 6.38%.

Melting Point (Perkin Elmer DSC7): 198° C.

Alternatively:

EXAMPLE 1A

[(1R,5R,6S)-6-(Aminomethyl)bicyclo[3.2.0]hept-6-yl]acetic acid hydrochloride

The nitro acid of preparation 32 (2.0 g; 9.4 mmol) in (either 1:1 IPA:H$_2$O or) 1:1 MeCN:H$_2$O (40 ml; 20 ml/g) was hydrogenated using 10% Pd/C (0.2 g; 0.1 g/g) at 50° C. and 60 psi for 18 hours. The reaction mixture was filtered through Celite and the filter pad washed with 1:1 IPA:H$_2$O or 1:1 MeCN:H$_2$O (20 ml). The combined filtrate and wash were concentrated under vacuum and azeotroped dry with further IPA or MeCN to yield the title compound as a white crystalline solid (1.52 g).

EXAMPLE 1B

[(1R,5R,6S)-6-(Aminomethyl)bicyclo[3.2.0]hept-6-yl]acetic acid hydrochloride

The lactam of preparation 33 (4.70 g, 28.44 mmol) and hydrochloric acid (57 ml of a 6N solution) were refluxed together for 6 h. The mixture was allowed to cool and then diluted with water (60 ml). The aqueous layer was washed with dichloromethane (2×100 ml), filtered and then evaporated under reduced pressure. The resulting off-white solid was triturated with ethyl acetate and recrystallised using acetonitrile:water 1:1 to give the title compound (4.51 g).

EXAMPLE 1C

[(1R,5R,6S)-6-(Aminomethyl)bicyclo[3.2.0]hept-6-yl]acetic acid (Zwitterion)

The amino acid hydrochloride of Example 1 (2.2 g) was dissolved in 7.25 ml H$_2$O (3.3 ml/g). The solution was adjusted to pH 7.5, initially with about 1.6 ml aq. NaOH, but finally with some drops of aqueous 0.1N aq. NaOH The precipitated zwitterion was stirred for 8 hours at 8° C. and the slurry filtered and the residues washed with ice-cold water (6 ml). The water-wet filter cake was slurried in IPA (15 ml) and refluxed for 10 minutes. After cooling to ambient temperature, the slurry was filtered, and the residues washed with IPA (5 ml). The filter cake was reslurried in IPA (15 ml), refluxed and cooled to ambient temperature. The slurry was filtered and the residues washed with IPA (5 ml) and dried under vacuum at 40° C. to constant weight to yield the title compound as a crystalline solid (1.4 g).

Melting Point (Perkin Elmer DSC7): 208° C.

EXAMPLE 2

[(1R,5R,6S)-6-(Aminomethyl)bicyclo[3.2.0]hept-6-yl]acetic acid hydrochloride

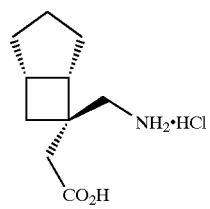

The isocyanate of preparation 12 (approx 11.0 mmol) and 6N hydrochloric acid (30 ml) were refluxed for 16 h. The mixture was allowed to cool, diluted with water (100 ml) and extracted with dichloromethane (2×50 ml). The aqueous phase was concentrated under reduced pressure to give a yellow solid and washed with ethyl acetate and acetonitrile to give 0.94 g of the title compound as a white solid.

$^1$H-NMR (400 MHz, $d_6$-DMSO): δ=7.94 (3H, br s), 3.15 (1H, d), 3.07 (1H, d), 2.72 (1H, quin), 2.46 (1H, m), 2.42 (1H, d), 2.33 (1H, d), 1.98 (1H, m), 1.80–1.64 (2H, m), 1.59 (1H, m), 1.48–1.28 (3H, m), 1.23 (1H, dd).

LRMS (APCI): m/z [(MH−HCl)⁺] 184.

LCMS (Prodigy ODS3 (3μ) 150 mm×4.6 mmid column, 20–100% Acetonitrile+0.1% formic acid) Retention Time= 4.34 min, 100% purity.

[α]$_D$(c=0.35 in methanol)=+13.0°

EXAMPLE 3

[(1R,5R,6S)-6-(Aminomethyl)bicyclo[3.2.0]hept-6-yl]acetic acid hydrochloride

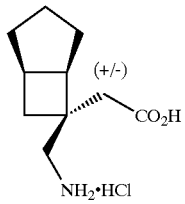

The isocyanate of preparation 17 (approx 2.79 mmol) and 6N hydrochloric acid (15 ml) were refluxed for 18 h. The mixture was allowed to cool, diluted with water (60 ml) and extracted with dichloromethane (3×50 ml). The aqueous phase was concentrated under reduced pressure to give a yellow solid which was washed with ethyl acetate and acetonitrile to give 0.45 g of the title compound as a white solid.

¹H-NMR (400 MHz, d₆-DMSO): δ=7.84 (3H, br s), 2.92 (1H, d), 2.85 (1H, d), 2.75 (1H, t), 2.69 (1H, d), 2.39 (1H, t), 1.81–1.62 (4H, m), 1.41–1.30 (4H, m).

LRMS (APCI): m/z [(MH−HCl)⁺] 184.

LCMS (Prodigy ODS3 (3μ) 150 mm×4.6 mmid column, 20–100% Acetonitrile+0.1% formic acid) Retention Time= 4.27 min, 99.8% purity.

EXAMPLE 4

[(1R,6R,7S)-7-(Aminomethyl)bicyclo[4.2.0]oct-7-yl]acetic acid hydrochloride

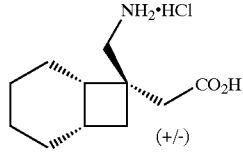

The lactam of preparation 22 (3.20 g, 17.9 mmol) was heated to reflux in 1,4-dioxane (15 ml) and 6N HCl (50 ml). After 4 hrs the mixture was cooled to room temperature and washed with dichloromethane (2×30 ml). The aqueous phase was collected and the solvent removed in vacuo. The residue was triturated with ethyl acetate and the resulting solid collected by filtration and dried under vacuum to give 2.74 g of the title compound as a white solid.

¹H-NMR (400 MHz, D₂O): 3.24 (2H, m), 2.58 (2H, s), 2.39 (1H, m), 2.03 (1H, m), 1.76 (2H, m) 1.59–1.10 (7H, m) 0.96 (1H, m).

LRMS (APCI): m/z [(MH−HCl)⁺] 198.

EXAMPLE 5

[(1R,6R,7S)-7-(Aminomethyl)bicyclo[4.2.0]oct-7-yl]acetic acid hydrochloride

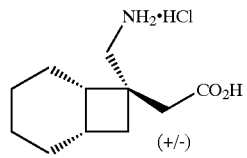

Diphenylphosphoryl azide (0.43 ml, 1.98 mmol) was added to a stirring solution of triethylamine (0.28 ml, 2.03 mmol) and the acid of preparation 29 (0.47 g, 1.96 mmol approx) in toluene (15 ml) at room temperature under nitrogen. The mixture was stirred for 16 hrs and then warmed to 35° C. for 1 hr. The mixture was allowed to cool, diluted with ethyl acetate (60 ml), washed with saturated aqueous sodium hydrogen carbonate (2×100 ml), brine, and dried (MgSO₄). The solvent was removed under reduced pressure and the resulting yellow oil was heated to reflux in 6N HCl (20 ml). After 18 hrs the mixture was cooled to room temperature and washed with dichloromethane (2×60 ml) and diethyl ether (60 ml). The aqueous phase was collected and the solvent removed in vacuo. The residue was triturated with ethyl acetate and the resulting solid collected by filtration and dried under vacuum to give 0.304 g of title compound as a white solid.

¹H-NMR (400 MHz, d₆-DMSO): 3.04 (1H, d), 2.99 (1H, d), 2.68 (1H, d) 2.62 (1H, d), 1.98 (1H, m), 1.83 (1H, t), 1.69–1.28 (9H, m), 1.00 (1H, m).

LRMS (APCI): m/z [(MH−HCl)⁺] 198.

Preparation 1

(1RS,5RS)-Bicyclo[3.2.0]heptan-6-one

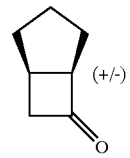

Palladium (1 g, 10% w/w on charcoal) was added to a solution of bicyclo[3.2.0]hept-2-en-6-one (12 ml, 111.3 mmol) in ethyl acetate (100 ml) and the mixture was hydrogenated for 6 hours at 30° C. and 483 kPa (70 p.s.i.). The reaction mixture was filtered and the solvent was evaporated under reduced pressure to give 12.1 g of the title compound as a colourless oil.

ν$_{max}$(film)/cm⁻¹ 1777.

¹H-NMR (400 MHz, CDCl₃): δ=3.54 (1H, m), 3.19 (1H, ddd), 2.88 (1H, m), 2.49 (1H, ddd), 2.04 (1H, m), 1.91–1.49 (5H, m).

Preparation 1A (1R,5R)-bicyclo[3.2.0]heptan-6-one

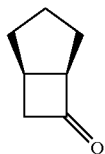

A solution of (1S,5R)-bicyclo[3.2.0]hept-2-en-6-one[1] (50.0 g; 462 mmol) in EtOAc (375 mL) was hydrogenated using 50% wet 5% Pd/C (5.0 g) at 60 psi for 8 hours at ambient temperature. The reaction mixture was filtered through Celite, and the filtrate concentrated under vacuum to yield 41.3 g of the title compound as a colourless oil.

$^1$H-NMR (400 MHz, CDCl$_3$): δ=3.55 (1H, m), 3.20 (1H, m), 2.90 (1H, m), 2.50 (1H, m), 2.0–1.5 (6H, m).

[1]Ref: EP0074856

Preparation 2

Ethyl (2E/Z)-(1RS,5RS)-bicyclo[3.2.0]hept-6-ylidene(cyano)ehanoate

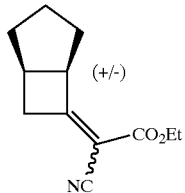

The ketone of preparation 1 (22.4 g, 204.1 mmol), ethyl cyanoacetate (21.7 ml, 204.1 mmol), ammonium acetate (15.7 g, 204.1 mmol) and glacial acetic acid (11.7 ml, 204.1 mmol) were refluxed in toluene (220 ml) using a Dean-Stark trap. After 8 h, the mixture was allowed to cool and diluted with ethyl acetate (300 ml), washed with water (3×150 ml), brine and dried (MgSO$_4$). The solvent was evaporated under reduced pressure. The residue was chromatographed (SiO$_2$, heptane/ethyl acetate, 95:5 to 7:3) to give 30 g of a 6:4 mixture of isomers of the title compound as a yellow solid.

ν$_{max}$(film)/cm$^{-1}$ 2225, 1725, 1640.

$^1$H-NMR (400 MHz, CDCl$_3$): δ(major isomer)=4.26 (2H, m)3.64 (1H, m), 3.36 (1H, ddd),2.96 (1H, m),2.70 (1H, dt), 2.11 (1H, m),1.92–1.58, 5H, m), 1.32 (3H, m); δ(minor isomer)=4.26 (2H, m),3.85 (1H, m), 3.15 (1H, ddd),2.96 (1H, m),2.52 (1H, dt, J20.0, 4.4),2.02 (1H, m), (1.92–1.58, 5H, m), 1.32 (3H, m).

LRMS (APCI): m/z [M−H]204.

Preparation 3

Ethyl[(1RS,5RS,6RS)-6-benzylbicyclo[3.2.0]hept-6-yl](cyano)acetate

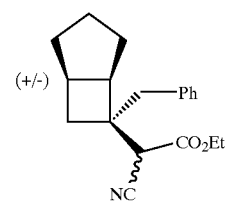

The cyanoester of preparation 2 (10.0 g, 48.7 mmol) in THF (60 ml) was added over 1 h to a stirring solution of benzylmagnesium chloride (78 ml of a 1M solution in ether, 78 mmol) in THF (100 ml) at −78° C. under argon. After stirring for 2 h at this temperature, the mixture was quenched by addition of saturated ammonium chloride solution (40 ml). The mixture was allowed to warm to room temperature, and dilute hydrochloric acid (150 ml) was added. The aqueous layer was extracted with ethyl acetate (3×100 ml). The combined organic layers were washed with brine, dried (MgSO$_4$) and the solvent was evaporated under reduced pressure to give the title compound as a mixture of diastereoisomers and as a yellow oil which was used crude in the next step.

ν$_{max}$(film)/cm$^{-1}$ 2247, 1741.

Preparation 4

[(1RS,5RS,6RS)-6-benzylbicyclo[3.2.0]hept-6-yl] acetic acid

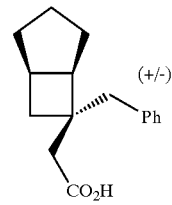

The mixture of the diastereomeric cyano-esters of preparation 3 (20.3 g, 68.4 mmol) and potassium hydroxide (23.0 g, 410.4 mmol) were heated to 160° C. in ethylene glycol (350 ml) for 38 h. After this time, the mixture was allowed to cool and dilute hydrochloric acid (300 ml) was added carefully. The mixture was extracted with ethyl acetate (3×200 ml) and the combined organic fractions were washed with brine, dried (MgSO$_4$) and the solvent was evaporated under reduced pressure. The residue was chromatographed (SiO$_2$, heptane/ethyl acetate, 8:2) to give 14.6 g of the racemic diastereomeric title compound as a white solid.

ν$_{max}$(film)/cm$^{-1}$ 3344, 1704.

$^1$H-NMR (400 MHz, CDCl$_3$): δ=7.31–7.22 (5H, m), 3.02 (1H, d), 2.97 (1H, d), 2.64 (2H, m), 2.34 (1H, d), 2.24 (1H, d), 2.13 (1H, m), 1.84–1.59 (3H, m), 1.50–1.32 (4H, m).

LRMS (APCI): m/z [M−H]243.

Preparation 5

[(1RS,5RS,6RS)-6-benzylbicyclo[3.2.0]hept-6-yl]
acetate acid

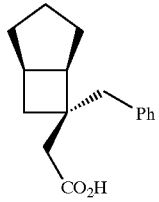

(R)-(+)-α-Methylbenzylamine (6.67 g, 55 mmol) was added to a stirring solution of racemic acid of preparation 4 (24 g, 98.2 mmol) dissolved in ethyl acetate. The acid salt precipitated out of the solution as a white solid. This was recrystallised three times from ethyl acetate to give 8.5 g of the acid salt. Further recrystallisation of the residue gave an additional batch of 8.5 g of the acid salt. The first batch of the salt was taken up in dichloromethane, washed with dilute hydrochloric acid, brine and dried (MgSO$_4$). The solvent was evaporated under reduced pressure to give 5.0 g of the title compound as a white solid.

HPLC [Chiralcel OD 250×4.6 mm column (Mobile phase: 90% hexane, 10% IPA cont. 0.5% TFA)]: Retention time=5.1 min (94% ee).

$[\alpha]_D$(c=1.13 in chloroform)=−20.2°

The second batch of the salt was taken up in dichloromethane, washed with dilute hydrochloric acid, brine and dried (MgSO$_4$) to give a further 5 g of acid of 86% ee.

Similarly prepared was:

Preparation 6

[(1RS,5RS,6RS)-6-benzylbicyclo[3.2.0]hept-6-yl]
(cyano)acetate

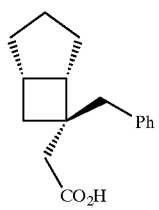

by recrystallisation of the salt generated by addition of (S)-(−)-α-methylbenzylamine.

HPLC [Chiralcel OD 250×4.6 mm column (Mobile phase: 90% hexane, 10% IPA cont. 0.5% TFA)]: Retention time=4.2 min (95% ee).

$[\alpha]_D$(c=1.0 in chloroform)=+17.3°

Preparation 7

Methyl [(1RS,5RS,6RS)-6-benzylbicyclo[3.2.0]
hept-6-yl]acetate

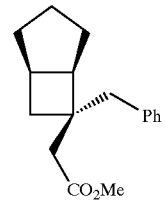

Trimethylsilyldiazomethane (17.7 ml of a 2M solution in hexane, 35.4 mmol) was added dropwise to a stirring solution of acid of preparation 5 (7.85 g, 32.1 mmol) in a mixture of toluene (90 ml) and methanol (22.5 ml) at 0° C. under argon. The mixture was allowed to warm to room temperature and stirred for 4 h. The solvent was removed under reduced pressure and the residue was taken up in ethyl acetate (150 ml), washed with saturated sodium hydrogen carbonate (150 ml), dilute hydrochloric acid (100 ml), brine and dried (MgSO$_4$). The solvent was evaporated under reduced pressure The residue was chromatographed (SiO$_2$, heptane/ethyl acetate, 9:1) to give 7.0 g of the title compound as a colourless oil.

$v_{max}$(film)/cm$^{-1}$ 1736.
$^1$H-NMR (400 MHz, CDCl$_3$): δ=7.28–7.21 (5H, m), 3.67 (3H, s), 2.97 (1H, d), 2.92 (1H, d), 2.65–2.60 (2H, m), 2.26 (1H, d), 2.18 (1H, d), 2.08 (1H, m), 1.82–1.52 (3H, m), 1.48–1.22 (4H, m).
LRMS (APCI): m/z [M−H]259.
$[\alpha]_D$(c=0.11 in methanol)=−24.1°

Preparation 8

[(1R,5R,6S)-6-(2-methoxy-2-oxoethyl)bicyclo[3.2.0]
hept-6-yl]acetic acid

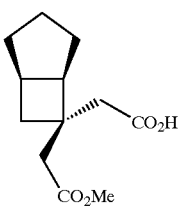

The ester of preparation 7 (7.0 g, 27.1 mmol) and sodium periodate (81.1 g, 379.3 mmol) were stirred together in ethyl acetate (100 ml), acetonitrile (100 ml) and water (150 ml) for 5 minutes. The mixture was cooled to 0° C. and ruthenium (III) chloride hydrate (0.11 g, 0.54 mmol) was added to the reaction mixture. The reaction was allowed to warm to room temperature and stirred for 24 h. Diethyl ether (150 ml) was added and the mixture was stirred for 40 minutes. Dilute hydrochloric acid (200 ml) was added to the mixture which was then extracted with ethyl acetate (3×100 ml). The combined organic fractions were washed with saturated sodium thiosulfate solution, brine, dried (MgSO$_4$) and the solvent was evaporated under reduced pressure to give the title compound as a yellow oil.

$v_{max}$(film)/cm$^{-1}$ 1733, 1715.
$^1$H-NMR (400 MHz, CDCl$_3$): δ=3.65 (3H, s), 2.82–2.76 (3H, m), 2.55–2.49 (3H, m), 2.05 (1H, m), 1.81 (1H, m), 1.73–1.69 (2H, m),1.49–1.28 (4H, m).
LRMS (APCI): m/z [M−H] 225.

Preparation 9

Methyl [(1R,5R,6S)-6-(Isocyanatomethyl)bicyclo[3.2.0]hept-6-yl]acetate

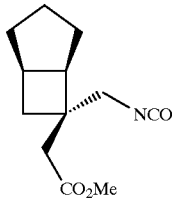

Diphenylphosphoryl azide (8.45 ml, 39.2 mmol) was added to a stirring solution of triethylamine (5.6 ml, 40.4 mmol) and the acid of preparation 8 (8.78 g, 38.8 mmol) in toluene (80 ml) at room temperature under nitrogen. The mixture was stirred for 3 hours and then warmed to 35° C. for 1.5 hours. The mixture was allowed to cool, diluted with ethyl acetate (150 ml), washed with saturated aqueous sodium hydrogen carbonate (150 ml), brine, and dried (MgSO$_4$). The solvent was removed under reduced pressure to give 8.7 g of the title compound as a yellow oil.

$\nu_{max}$(film)/cm$^{-1}$ 2265, 2171, 1733.

Preparation 10

Methyl [(1S,5S,6R)-6-benzylbicyclo[3.2.0]hept-6-yl]acetate

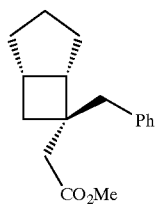

Trimethylsilyldiazomethane (5.7 ml of a 2M solution in hexane, 11.4 mmol) was added dropwise to a stirring solution of the acid of preparation 6 (2.77 g, 11.3 mmol) in a mixture of toluene (30 ml) and methanol (7.5 ml) at 0° C. under argon. The mixture was allowed to warm to room temperature and stirred for 4 h. The solvent was removed under reduced pressure and the residue was taken up in ethyl acetate (100 ml), washed with saturated sodium hydrogen carbonate (100 ml), dilute hydrochloric acid (100 ml), brine and dried (MgSO$_4$). The solvent was evaporated under reduced pressure The residue was chromatographed (SiO$_2$, heptane/ethyl acetate, 9:1) to give 2.84 g of the title compound as a colourless oil.

$^1$H-NMR (400 MHz, CDCl$_3$): δ=7.28–7.21 (5H, m), 3.67 (3H, s), 2.97 (1H, d), 2.92 (1H, d,), 2.65–2.60 (2H, m), 2.26 (1H, d), 2.18 (1H, d), 2.08 (1H, m), 1.82–1.52 (3H, m), 1.48–1.22 (4H, m);

[α]$_D$(c=0.11 in methanol)=+23.1°

Preparation 11

[(1S,5S,6R)-6-(2-methoxy-2-oxoethyl)bicyclo[3.2.0]hept-6-yl]acetic acid

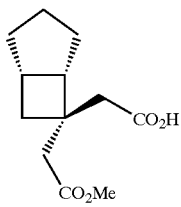

The ester of preparation 10 (7.0 g, 27.1 mmol) and sodium periodate (81.1 g, 379.3 mmol) were stirred together in ethyl acetate (100 ml), acetonitrile (100 ml) and water (150 ml) for 5 minutes. The mixture was cooled to 0° C. and ruthenium (III) chloride hydrate (0.11 g, 0.54 mmol) was added to the reaction mixture. The reaction was allowed to warm to room temperature and stirred for 24 h. Diethyl ether (150 ml) was added and the mixture was stirred for 40 minutes. Dilute hydrochloric acid (200 ml) was added to the mixture which was then extracted with ethyl acetate (3×100 ml). The combined organic fractions were washed with saturated sodium thiosulfate solution, brine, dried (MgSO$_4$) and the solvent was evaporated under reduced pressure to give the title compound as a yellow oil.

$^1$H-NMR (400 MHz; CDCl$_3$): δ=3.65 (3H, s), 2.82–2.76 (3H, m), 2.55–2.49 (3H, m), 2.05 (1H, m), 1.81 (1H, m), 1.73–1.69 (2H, m), 1.49–1.28 (4H, m).

Preparation 12

Methyl [(1S,5S,6R)-6-(isocyanatomethyl)bicyclo[3.2.0]hept-6-yl]acetate

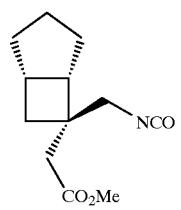

Diphenylphosphoryl azide (2.4 ml, 11.1 mmol) was added to a stirring solution of triethylamine (1.6 ml, 11.4 mmol) and the acid of preparation 11 (11.0 mmol approx) in toluene (30 ml) at room temperature under nitrogen. The mixture was refluxed for 2 hours. The mixture was allowed to cool, diluted with ethyl acetate (150 ml), washed with saturated aqueous sodium hydrogen carbonate (2×150 ml), brine, and dried (MgSO$_4$). The solvent was removed under reduced pressure to give the title compound as a yellow oil.

$\nu_{max}$ (film)/cm$^{-1}$ 2265, 2151, 1734.

Preparation 13 tert-butyl [(1RS,5RS,6SR)-6-benzylbicyclo[3.2.0]hept-6-yl]acetate

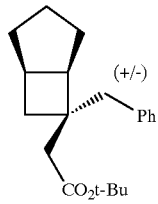

Oxalyl chloride (0.92 ml, 10.5 mmol) was added dropwise to a stirring solution of the acid of preparation 4 (2.34 g, 9.58 mmol) in dichloromethane (30 ml) under argon at 0° C. Dimethylformamide (0.3 ml) was carefully added and the mixture was allowed to warm to room temperature and stirred for a further 4 hours. The solvent was removed in vacuo and the residue diluted with dichloromethane (20 ml). 2-Methyl propan-1-ol (10 ml) in dichloromethane (20 ml) was carefully added to the reaction mixture under argon followed by diisopropylethylamine (2.5 ml, 14.4 mmol). The mixture was stirred for 17 hours and then taken up in ethyl acetate, washed with saturated aqueous sodium hydrogen carbonate (2×200 ml), and dried (MgSO$_4$). The solvent was removed under reduced pressure and the residue was chromatographed (SiO$_2$, heptane/ethyl acetate 95:5) to give the title compound (2.40 g) as a yellow oil.

$v_{max}$(film)/cm$^{-1}$ 1727.

$^1$H-NMR (400 MHz, CDCl$_3$): δ=7.28–7.21 (5H, m, Ph), 2.98 (1H, d), 2.92 (1H, d), 2.64–2.56 (2H, m), 2.16 (1H, d), 2.09 (1H, d), 2.04 (1H, m), 1.80–1.50(3 H, m), 1.48 (9H, s), 1.47–1.20 (4H, m).

Preparation 14

[(1RS,5RS,6SR)-6-(2-tert-Butoxy-2-oxoethyl)bicyclo[3.2.0]hept-6-yl]acetic acid

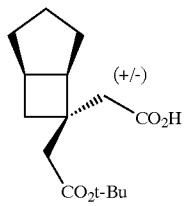

The ester of preparation 13 (2.4 g, 7.99 mmol) and sodium periodate (23.93 g, 111.8 mmol) were stirred together in ethyl acetate (24 ml), acetonitrile (24 ml) and water (36 ml) for 5 minutes. The mixture was cooled to 0° C. and ruthenium (III) chloride hydrate (0.033 g, 0.16 mmol) was added to the reaction mixture. The reaction was allowed to warm to room temperature and stirred for 24 h. Diethyl ether (60 ml) was added and the mixture was stirred for 40 minutes. Dilute hydrochloric acid (150 ml) was added to the mixture which was then extracted with ethyl acetate (3×100 ml). The combined organic fractions were washed with brine, dried (MgSO$_4$) and the solvent was evaporated under reduced pressure to give the title compound (1.78 g, 83%) as a yellow oil.

$v_{max}$(film)/cm$^{-1}$ 1728, 1714.

$^1$H-NMR (400 MHz, CDCl$_3$): δ=2.78 (1H, d), 2.71 (1H, d), 2.43 (1H, d), 2.38 (1H, d), 2.01 (1H, m), 1.86–1.64 (3H, m), 1.52–1.36 (6H, m), 1.45 (9H, s).

LRMS (APCI): m/z [M−H] 267.

Preparation 15

(1RS,5RS,6SR)-6-(2-tert-Butoxy-2-oxoethyl)bicyclo[3.2.0]hept-6-yl]acetic acid methyl ester

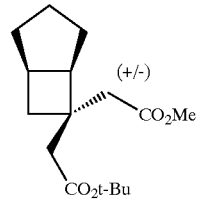

Trimethylsilyldiazomethane (4.3 ml of a 2M solution in hexane, 8.6 mmol) was added dropwise to a stirring solution of the acid of preparation 14 (1.78 g, 6.63 mmol) in a mixture of toluene (24 ml) and methanol (6 ml) at 0° C. under argon. The mixture was allowed to warm to room temperature and stirred for 24 h. The solvent was removed under reduced pressure and the residue was taken up in ethyl acetate (100 ml), washed with saturated sodium hydrogen carbonate (100 ml), dilute hydrochloric acid (100 ml), brine and dried (MgSO$_4$). The solvent was evaporated under reduced pressure to give the title compound as a yellow oil.

$v_{max}$ (film)/cm$^{-1}$ 1732.

LRMS (APCI): m/z [M−M$^t$Bu] 209.

Preparation 16

[(1RS,5RS,6RS)-6-(2-Methoxy-2-oxoethyl)bicyclo[3.2.0]hept-6-yl]acetic acid

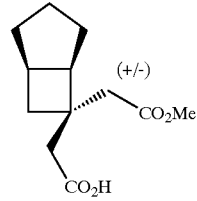

Trifluoroacetic acid (5 ml) was added dropwise to a stirring solution of the ester of preparation 15 (approx. 6.63 mmol) in dichloromethane (15 ml) at 0° C. The mixture was allowed to warm to room temperature and stirred for a further 17 hours. The mixture was washed with saturated aqueous sodium hydrogen carbonate solution until it reached neutral pH and extracted with dichloromethane (50 ml). It was then reacidified to pH 4 with dilute hydrochloric acid. The mixture was then further extracted with dichloromethane (2×50 ml). The combined organic fractions were washed with brine, dried (MgSO$_4$) and the solvent removed under reduced pressure. The residue was purified by chromatography (SiO$_2$, 8:2 to 6:4 heptane/ethyl acetate) to give 0.63 g of the title compound as a colourless oil.

$v_{max}$(film)/cm$^{-1}$ 3200, 1738, 1705.

$^1$H-NMR (400 MHz, CDCl$_3$): δ=3.68 (3H, s), 2.84–2.73 (3H, m), 2.61–2.48 (3H, m), 2.03 (1H, m), 1.80 (1H, m), 1.79–1.32 (6H, m).

LRMS (APCI): m/z [M−H] 225.

Preparation 17

Methyl [(1RS,5RS,6RS)-6-(isocyanatomethyl)bicyclo[3.2.0]hept-6-yl]acetate

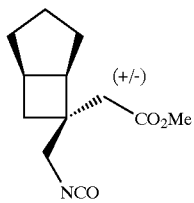

Diphenylphosphoryl azide (0.61 ml, 2.82 mmol), triethylamine (0.40 ml, 2.90 mmol), and the acid of preparation 16 (0.63 g, 2.79 mmol) were refluxed in toluene (15 ml) for 6 h. The mixture was allowed to cool and diluted with ethyl acetate (60 ml). The resulting solution was washed with saturated aqueous sodium hydrogen carbonate (150 ml), brine, and dried (MgSO$_4$). The solvent was removed under reduced pressure to give the title compound as a yellow oil.

R$_f$(heptane-ethyl acetate, 9:1) 0.36.

$v_{max}$ (film)/cm$^{-1}$ 2259, 2171, 1736.

Preparation 18

(1RS,6SR)-8,8-Dichlorobicyclo[4.2.0]octan-7-one

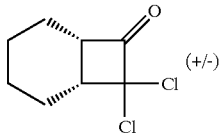

Copper (II) sulphate (2.0 g, 8.0 mmol) was dissolved in water (75 ml) and added to zinc dust (30 g). The mixture was stirred for 2 hours. The mixture was filtered and the solid collected, washed twice with acetone and dried under vacuum at 100° C. for 24 hrs. A portion of the activated zinc (8.0 g) was added to a solution of cyclohexene (10 ml, 98.9 mmol) in diethyl ether (180 ml). Trichloroacetyl chloride (10.48 ml, 93.96 mmol) in diethyl ether (20 ml) was added at such a rate to keep the mixture at reflux. After the addition was complete, the mixture was heated to reflux for 4 hrs. The mixture was cooled to room temperature, diluted with diethyl ether (50 ml) and carefully poured into an aqueous saturated solution of sodium bicarbonate. The mixture was acidified with 2N HCl and the organic phase separated. The ether extract was washed with water and then with saturated aqueous sodium bicarbonate. The organic phase was collected, dried (MgSO$_4$) and the solvent removed under reduced pressure. The residue was purified by flash chromatography (silica, EtOAc:Heptane 1:9) to give 8.62 g of the title compound as a clear oil.

$v_{max}$(film)/cm$^{-1}$ 2939, 1802.

$^1$H-NMR (400 MHz, CDCl$_3$): δ=3.94 (1H, m), 2.95 (1H, m), 2.18–1.82 (2H, m), 1.80–1.20 (6H, m).

Preparation 19

(1RS,6RS)-Bicyclo[4.2.0]octan-7-one

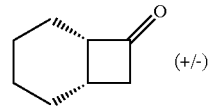

(1RS,6SR)-8,8-dichlorobicyclo[4.2.0]octan-7-one (preparation 18) (8.60 g, 44.6 mmol) was heated to reflux in acetic acid (100 ml) with zinc dust (29.0 g, 446 mmol). After 4 hrs the mixture was cooled to room temperature, diluted with diethyl ether (200 ml) and washed with 2N NaOH (2×100 ml) and then with saturated aqueous NaHCO$_3$ (4×100 ml). The ether phase was collected, dried (MgSO$_4$) and the solvent was removed under reduced pressure to give 4.79 g of the title compound as a clear oil.

$v_{max}$(film)/cm$^{-1}$ 2930, 1776.

$^1$H-NMR (400 MHz, CDCl$_3$): δ=3.27 (1H, m), 3.12 (1H, m), 2.42 (2H, m), 2.20–1.02 (8H, m).

Preparation 20

Ethyl (2Z/E)-(1RS,6RS)-bicyclo[4.2.0]oct-7-ylideneethanoate

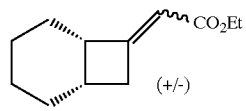

Sodium hydride (60% dispersion in oil, 1.46 g, 36.6 mmol) was suspended in dry tetrahydrofuran (150 ml) and cooled to 0° C. Triethylphosphonoacetate (7.65 ml, 38.5 mmol) was added and the mixture stirred at 0° C. for 15 mins. A solution of(1RS,6RS)-bicyclo[4.2.0]octan-7-one (preparation 19) (4.78 g, 38.5 mmol) in THF (20 ml) was then added and the mixture stirred at 0° C. After 1 hr the mixture was allowed to warm to room temperature, diluted with ethyl acetate (200 ml) and washed with 2N HCl (2×150 ml). The organic phase was collected, dried (MgSO$_4$) and the solvent removed under reduced pressure. The residue was purified by flash chromatography (Silica, EtOAc:Heptane 3:20) to give 5.49 g of the title compound as a clear oil.

$v_{max}$(film)/cm$^{-1}$ 2929, 1715, 1186.

$^1$H-NMR (400 MHz, CDCl$_3$): δ=5.63 and 5.58 (1H in total–E/Z isomers, 2×m), 4.15 (2H, m), 3.38–2.98 (2H, m), 2.79–2.35 (2H, m), 2.13–1.05 (11H, m).

LRMS (APCI): m/z [MH$^+$] 195.

Preparation 21

Ethyl [(1RS,6RS,7SR)-7-(nitromethyl)bicyclo[4.2.0]oct-7-yl]acetate

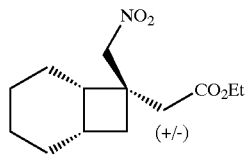

(2Z/E)-(1RS,6RS)-Bicyclo[4.2.0]oct-7-ylideneethanoate (preparation 20) (5.47 g, 28.2 mmol) was heated to 60° C.

in tetrahydrofuran (50 ml) with nitromethane (3.05 ml, 56.4 mmol) and tetrabutylammonium fluoride (1M in THF, 42 ml, 42.0 mmol). After 18 hrs the mixture was cooled to room temperature, diluted with ethyl acetate (200 ml) and washed with 2N HCl (2×100 ml) and then with brine. The organic phase was collected, dried (MgSO$_4$) and the solvent removed in vacuo. The residue was purified by flash chromatography (silica, EtOAc:heptane 1:9) to give 4.73 g of the title compound as a clear oil.

$v_{max}$(film)/cm$^{-1}$ 1182, 1547, 1731, 2936.

$^1$H-NMR (400 MHz, CDCl$_3$): δ=4.83 (2H, m), 4.12 (2H, q), 2.66 (2H, m), 2.57 (1H, m), 2.22 (1H, m), 2.05 (1H, m), 1.86 (1H, m), 1.76–1.31 (7H, m), 1.26 (3H, t), 1.10 (1H, m).

LRMS (APCI): m/z [MH$^+$] 256.

Preparation 22

(1S,6S,7R)-Spiro[bicyclo[4.2.0]octane-7,3'-pyrrolidin]-5'-one

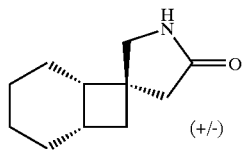

Ethyl [(1RS,6RS,7SR)-7-(nitromethyl)bicyclo[4.2.0]oct-7-yl]acetate (preparation 21) (4.70 g, 18.4 mmol) was shaken in methanol (150 ml) at 30° C. over Raney Nickel catalyst under an atmosphere of hydrogen gas at 483 kPa (70 p.s.i.). After 4 hrs the catalyst was removed by filtration through celite and the solvent removed under reduced pressure to give 3.23 g of the title compound as a clear oil which solidified on standing.

$v_{max}$(film)/cm$^{-1}$ 2919, 1712, 1677.

$^1$H-NMR (400 MHz, CDCl$_3$): δ=5.61 (1H, br. s), 3.46 (2H, m), 2.42 (2H, m), 2.18–1.01 (12H, m).

LRMS (APCI): m/z [MH$^+$] 180.

Preparation 23

Ethyl (2E/Z)-(1RS,6RS)-bicyclo[4.2.0]oct-7-ylidene(cyano)ethanoate

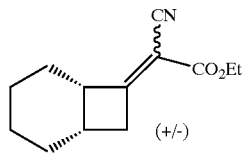

The ketone of preparation 19 (2.85 g, 23.0 mmol), ethyl cyanoacetate (2.45 ml, 23.0 mmol), ammonium acetate (1.77 g, 23.0 mmol) and glacial acetic acid (1.32 ml) were refluxed in toluene (40 ml) using a Dean-Stark trap. After 6 h, the mixture was allowed to cool and diluted with ethyl acetate (150 ml), washed with water (50 ml), brine and dried (MgSO$_4$). The solvent was evaporated under reduced pressure. The residue was chromatographed (SiO$_2$, heptane/ethyl acetate, 4:1) to give 2.76 g of a mixture of cyano-esters as a yellow solid.

$^1$H-NMR (400 MHz, CDCl$_3$): δ(major isomer); 4.26 (2H, q), 3.36 (1H, m), 3.02 (2H, m), 2.58 (1H, m), 1.30–2.18 (8H, m), 1.33 (3H, t).

δ(minor isomer)=4.25 (2H, q), 3.48 (1H, m), 3.23 (2H, m), 2.58 (1H, m), 1.30–2.18 (8H, m), 1.32 (3H, t).

Preparation 24

Ethyl [(1RS,6RS,7RS)-7-benzylbicyclo[4.2.0]oct-7-yl](cyano)acetate

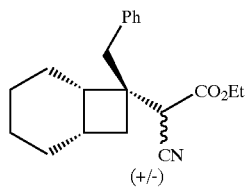

The cyanoester of preparation 23 (2.75 g, 12.5 mmol) in THF (60 ml) was added over 1 h to a stirring solution of benzylmagnesium chloride (20 ml of a 1M solution in ether, 20 mmol) in THF (20 ml) at −78° C. under argon. After stirring for 2 h at this temperature, the mixture was quenched by addition of saturated ammonium chloride solution (10 ml). The mixture was allowed to warm to room temperature, and dilute hydrochloric acid (30 ml) was added. The aqueous layer was extracted with ethyl acetate (3×40 ml). The combined organic layers were washed with brine, dried (MgSO$_4$) and the solvent was evaporated under reduced pressure to give a mixture of diastereomeric cyano-esters. The residue was chromatographed (SiO$_2$, heptane/ethyl acetate, 4:1) to give 3.53 g of a mixture of diastereomeric cyano-esters as a clear oil.

$R_f$(heptane-ethyl acetate, 4:1)=0.30

$v_{max}$(film)/cm$^{-1}$ 2247, 1740.

Preparation 25

[(1RS,6RS,7SR)-7-benzylbicyclo[4.2.0]oct-7-yl] acetic acid

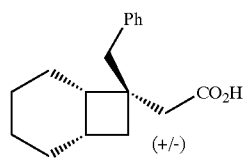

The mixture of diastereomeric cyano-esters of preparation 24 (3.52 g, 11.3 mmol) and potassium hydroxide (3.8 g, 67.9 mmol) were heated to 160° C. in ethylene glycol (75 ml) for 72 h. After this time, the mixture was allowed to cool and dilute hydrochloric acid was added carefully until the solution was acidic by pH paper. The mixture was extracted with ethyl acetate (3×100 ml) and the combined organic fractions were washed with brine, dried (MgSO$_4$) and the solvent was evaporated under reduced pressure. The residue was chromatographed (SiO$_2$, ethyl acetate:heptane 1:4) to give 2.11 g of the racemic diastereomeric acid as a yellow oil.

$^1$H-NMR (400 MHz, CDCl$_3$): δ=7.31–7.22 (5H, m), 3.08 (1H, d), 3.00 (1H, d), 2.56 (1H, m), 2.44 (1H, d), 2.38 (1H, d), 2.25 (1H, m), 1.98 (1H, m), 1.75 (1H, t), 1.71–1.30 (7H, m), 1.10 (1H, m).

LRMS (ES$^-$): m/z [M−H] 257.

Preparation 26 tert-butyl [(1RS,6RS,7SR)-7-benzylbicyclo[4.2.0]oct-7-yl]acetate

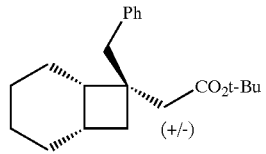

Oxalyl chloride (0.67 ml, 7.62 mmol) was added dropwise to a stirring solution of the acid of preparation 25 (1.79 g, 6.93 mmol) in dichloromethane (25 ml) under nitrogen at 0° C. Dimethylformamide (0.25 ml) was carefully added and the mixture was allowed to warm to room temperature and stirred for a further 4 hours. The solvent was removed in vacuo and the residue diluted with dichloromethane (20 ml). 2-Methyl propan-1-ol (9 ml) in dichloromethane (20 ml) was carefully added to the reaction mixture under argon followed by diisopropylethylamine (1.8 ml, 10.4 mmol). The mixture was stirred for 18 hours and then saturated aqueous sodium hydrogen carbonate (30 ml) was added. The mixture was extracted with ethyl acetate (3×50 ml) and the combined organic fractions were washed with brine and dried (MgSO$_4$). The solvent was removed under reduced pressure and the residue was chromatographed (SiO$_2$, heptane/ethyl acetate 98:2) to give ester (2.42 g).

$^1$H-NMR (400 MHz, CDCl$_3$): δ=7.33–7.19 (5H, m), 3.05 (1H, d), 2.96 (1H, d), 2.53 (1H, m), 2.30–2.18 (3H, m), 1.90 (1H, m), 1.72 (1H, t), 1.65–1.55 (2H, m), 1.48 (9H, s), 1.47–1.00 (6H, m).

Preparation 27

[(1RS,6RS,7SR)-7-(2-tert-Butoxy-2-oxoethyl)bicyclo[4.2.0]oct-7-yl]acetic acid

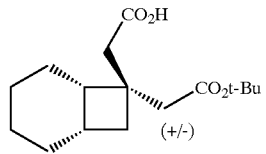

The ester of preparation 26 (6.93 mmol) and sodium periodate (20.75 g, 97.02 mmol) were stirred together in ethyl acetate (20 ml), acetonitrile (20 ml) and water (30 ml) for 5 minutes. The mixture was cooled to 0° C. and ruthenium (III) chloride hydrate (0.03 g, 0.14 mmol) was added to the reaction mixture. The reaction was allowed to warm to room temperature and stirred for 24 h. Diethyl ether (100 ml) was added and the mixture was stirred for 40 minutes. Dilute hydrochloric acid (150 ml) was added to the mixture which was then extracted with ethyl acetate (3×100 ml). The combined organic fractions were washed with brine, dried (MgSO$_4$) and the solvent was evaporated under reduced pressure to give 0.64 g of acid.

$^1$H-NMR (400 MHz, CDCl$_3$): δ=2.84 (1H, d), 2.75 (1H, d), 2.61–2.48 (3H, m), 2.17 (1H, m), 1.95–1.80 (3H, m), 1.78–1.30 (7H, m), 1.44 (9H, s).

Preparation 28

[(1RS,6RS,7SR)-6-(2-tert-Butoxy-2-oxoethyl)bicyclo[4.2.0]oct-7-yl]acetic acid methyl ester

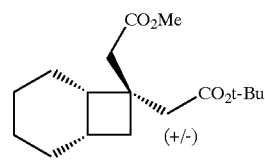

Trimethylsilyldiazomethane (1.2 ml of a 2M solution in hexane, 2.4 mmol) was added dropwise to a stirring solution of the acid of preparation 27 (0.64 g, 2.28 mmol) in a mixture of toluene (10 ml) and methanol (2.5 ml) at 0° C. under argon. The mixture was allowed to warm to room temperature and stirred for 16 h. The solvent was removed under reduced pressure and the residue was taken up in ethyl acetate (150 ml), washed with saturated sodium hydrogen carbonate (100 ml), dilute hydrochloric acid (100 ml), brine and dried (MgSO$_4$). The solvent was evaporated under reduced pressure to give 0.65 g of ester as a yellow oil.

$^1$H-NMR (400 MHz, CDCl$_3$): δ=3.66 (3H, s), 2.83 (1H, d), 2.74 (1H, d), 2.57 (1H, d), 2.49 (1H, d), 2.15 (1H, m), 1.94–1.78 (3H, m), 1.72–1.06 (8H, m), 1.43 (9H, s).

Preparation 29

[(1RS,6RS,7SR)-7-(2-Methoxy-2-oxoethyl)bicyclo[4.2.0]oct-7-yl]acetic acid

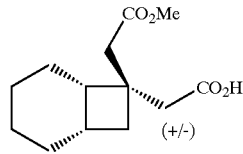

Trifluoroacetic acid (3 ml) was added dropwise to a stirring solution of the ester of preparation 28 (0.65 g, 2.19 mmol) in dichloromethane (9 ml) at 0° C. The mixture was allowed to warm to room temperature and stirred for a further 16 hours. The mixture was washed with saturated aqueous sodium hydrogen carbonate solution and then extracted with ethyl acetate (50 ml). The aqueous layer was acidified to pH 4 with dilute hydrochloric acid and then extracted with ethyl acetate (2×50 ml). The combined organic fractions were washed with brine, dried (MgSO$_4$) and the solvent removed under reduced pressure. The residue was purified by chromatography (SiO$_2$, 6:4 heptane/ethyl acetate) to give 0.47 g of acid as a yellow oil.

$^1$H-NMR (400 MHz, CDCl$_3$): δ=3.67 (3H, s), 2.84 (1H, d), 2.78 (1H, d), 2.74 (1H, d), 2.66 (1H, d), 2.49 (1H, m), 2.14 (1H, m), 1.95–1.81 (2H, m), 1.70 (1H, m), 1.63 (1H, m), 1.55–1.30 (5H, m), 1.07 (1H, m).

Preparation 30

Ethyl (2E)-(1R,5R)-bicyclo[3.2.0]hept-6-ylidene acetate/ethyl (2Z)-(1R,5R)-bicyclo[3.2.0]hept-6-ylidene acetate

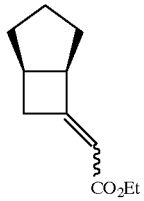

A solution of triethylphosphonoacetate (53.4 g; 238.3 mmol) in THF (25 mL) was added to a suspension of 60% sodium hydride dispersion (9.53 g; 238.3 mmol) in THF (75 mL) maintaining the temperature between 5–15° C. A solution of (1R,5R)-bicyclo[3.2.0]heptan-6-one (preparation 1A) (25 g, 226.9 mmol) in THF (150 ml) was added maintaining the temperature between 5–15° C. The reaction mixture was stirred at ambient temperature for 30 minutes then water (100 mL) added. The phases were separated and the organic layer containing the title compound was used directly in the next step.

$^1$H-NMR (400 MHz, CDCl$_3$): δ=5.55 (1H, d), 4.15 (2H, q), 3.40 (1H, m), 3.20 (1H, m), 2.90 (1H, m), 2.55 (1H, m), 1.8–1.5 (5H, m), 1.30 (3H, t).

Preparation 31

Ethyl (1R,5R,6S)-[6-(nitromethyl)bicyclo[3.2.0]hept-6-yl]acetate

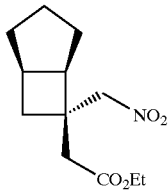

The THF solution of the compound of preparation 30 (assuming 40.9 g of compound in a total volume of 225 mL) was diluted with THF (270 ml). TBAF.3H$_2$O (93.1 g; 295.0 mmol) and MeNO$_2$ (453.9 mmol) were added and the solution heated at reflux for 4 hours. The reaction mixture was cooled and concentrated under reduced pressure. Toluene (330 mL) was added and the biphasic mixture washed with water (165 mL), 2M aq. HCl (165 mL+100 mL) and then further water (165 mL). The product-containing toluene layer was dried over MgSO$_4$ and concentrated under reduced pressure to give the title compound as a red/brown oil (90% (over 2 steps)).

$^1$H-NMR (400 MHz, CDCl$_3$): δ=4.80 (2H, m), 4.15 (2H, m), 2.85 (1H, m), 2.65 (1H, m), 2.55 (2H, m), 2.20 (1H, m), 1.9–1.4 (7H,m), 1.25 (3H, t).

Preparation 32

(1R,5R,6S)-[6-(nitromethyl)bicyclo[3.2.0]hept-6-yl] acetic acid

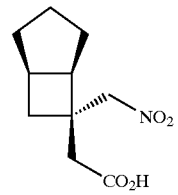

A solution of the nitro ester of preparation 31 (200 g; 828.9 mmol) in THF (1.0 L) was combined with 2M aq. NaOH (1.04L; 2.08 mol) and stirred at ambient temperature for 18 hours. The biphasic mixture was diluted with toluene (500 mL) and the layers separated. The aqueous was adjusted to pH 1–3 with conc. aq. HCl and extracted with CH$_2$Cl$_2$ (1.0 L+600 mL). The combined product-containing CH$_2$Cl$_2$ layers were concentrated under reduced pressure to yield the title compound as an orange oil, which set to a solid (163.4 g).

$^1$H-NMR (400 MHz, CDCl$_3$): δ=4.80 (2H, m), 2.85 (1H, m), 2.60 (3H, m), 2.20 (1H, m), 1.85 (1H, m), 1.70 (2H, m), 1.6–1.4(4H, m).

Preparation 33

(1RS,5RS,6SR)-Spiro[bicyclo[3.2.0]heptane-6,3'-pyrrolidin]-5'-one

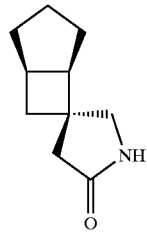

The nitroester of preparation 31 (13.0 g, 53.9 mmol) was shaken in methanol (125 ml) at 25° C. over Nickel sponge catalyst under an atmosphere of hydrogen gas at 345 kPa (50 p.s.i.). After 24 hrs the catalyst was removed by filtration through Arbocel and the solvent evaporated under reduced pressure. The residue was then chromatographed (SiO$_2$, ethyl acetate) to give the lactam (4.76 g).

$^1$H-NMR (400 MHz, CDCl$_3$): δ=5.86 (1H, br. s), 3.40 (2H, s), 2.79–2.70 (1H, m), 2.54–2.47 (1H, m), 2.32 (1H, d), 2.12 (1H, t), 2.03 (1H, d), 1.86–1.60 (3H, m), 1.57–1.38 (4H, m).

Microanalysis: Found: C, 72.48; H, 9.15; N, 8.43. C$_{10}$H$_{15}$NO requires C, 72.69; H, 9.15; N, 8.48%.

[α]$_D$ −28.4° (25° C.)

Pharmaceutical Composition Examples

In the following Examples, the active compound can be any compound of formula I-XXV and/or a pharmaceutically acceptable salt, solvate, or physiologically functional derivative thereof.

(i) Tablet Compositions

The following compositions A and B can be prepared by wet granulation of ingredients (a) to (c) and (a) to (d) with a solution of povidone, followed by addition of the magnesium stearate and compression.

|  | mg/tablet | mg/tablet |
| --- | --- | --- |
| Composition A | | |
| (a) Active ingredient | 250 | 250 |
| (b) Lactose B.P. | 210 | 26 |
| (c) Sodium Starch Glycollate | 20 | 12 |
| (d) Povidone B.P. | 15 | 9 |
| (e) Magnesium Stearate | 5 | 3 |
| | 500 | 300 |
| Composition B | | |
| (a) Active ingredient | 250 | 250 |
| (b) Lactose 150 | 150 | — |
| (c) Avicel PH 101 | 60 | 26 |
| (d) Sodium Starch Glycollate | 20 | 12 |
| (e) Povidone B.P. | 15 | 9 |
| (f) Magnesium Stearate | 5 | 3 |
| | 500 | 300 |
| Composition C | | |
| Active ingredient | 100 | |
| Lactose | 200 | |
| Starch | 50 | |
| Povidone | 5 | |
| Magnesium Stearate | 4 | |
| | 359 | |

The following compositions D and E can be prepared by direct compression of the admixed ingredients. The lactose used in formulation E is of the direct compression type.

|  | mg/tablet |
| --- | --- |
| Composition D | |
| Active ingredient | 250 |
| Magnesium Stearate | 4 |
| Pregelatinised Starch NF15 | 146 |
| | 400 |
| Composition E | |
| Active ingredient | 250 |
| Magnesium Stearate | 5 |
| Lactose | 145 |
| Avicel | 100 |
| | 500 |
| Composition F (Controlled release composition) | |
| (a) Active ingredient | 500 |
| (b) Hydroxypropylmethylcellulose (Methocel K4M Premium) | 112 |
| (c) Lactose B.P. | 53 |
| (d) Povidone B.P.C. | 28 |
| (e) Magnesium Stearate | 7 |
| | 700 |

The composition can be prepared by wet granulation of ingredients (a) to (c) with a solution of povidone, followed by addition of the magnesium stearate and compression.

Composition G (Enteric-coated Tablet)

Enteric-coated tablets of Composition C can be prepared by coating the tablets with 25 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

Composition H (Enteric-coated Controlled Release Tablet)

Enteric-coated tablets of Composition F can be prepared by coating the tablets with 50 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudgragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

(ii) Capsule Compositions

Composition A

Capsules can be prepared by admixing the ingredients of Composition D above and filling two-part hard gelatin capsules with the resulting mixture. Composition B (infra) may be prepared in a similar manner.

|  | mg/capsule |
| --- | --- |
| Composition B | |
| (a) Active ingredient | 250 |
| (b) Lactose B.P. | 143 |
| (c) Sodium Starch Glycollate | 25 |
| (d) Magnesium Stearate | 2 |
| | 420 |
| Composition C | |
| (a) Active ingredient | 250 |
| (b) Macrogol 4000 BP | 350 |
| | 600 |

Capsules can be prepared by melting the Macrogol 4000 BP, dispersing the active ingredient in the melt and filling two-part hard gelatin capsules therewith.

| Composition D | mg/capsule |
| --- | --- |
| Active ingredient | 250 |
| Lecithin | 100 |
| Arachis Oil | 100 |
| | 450 |

Capsules can be prepared by dispersing the active ingredient in the lecithin and arachis oil and filling soft, elastic gelatin capsules with the dispersion.

| Composition E (Controlled release capsule) | mg/capsule |
| --- | --- |
| (a) Active ingredient | 250 |
| (b) Microcrystalline Cellulose | 125 |
| (c) Lactose BP | 125 |
| (d) Ethyl Cellulose | 13 |
| | 513 |

The controlled release capsule formulation can be prepared by extruding mixed ingredients (a) to (c) using an extruder, then spheronising and drying the extrudate. The dried pellets are coated with a release controlling membrane (d) and filled into two-part, hard gelatin capsules.

| Composition F (Enteric capsule) | mg/capsule |
|---|---|
| (a) Active ingredient | 250 |
| (b) Microcrystalline Cellulose | 125 |
| (c) Lactose BP | 125 |
| (d) Cellulose Acetate Phthalate | 50 |
| (e) Diethyl Phthalat | 5 |
| | 555 |

The enteric capsule composition can be prepared by extruding mixed ingredients (a) to (c) using an extruder, then spheronising and drying the extrudate. The dried pellets are coated with an enteric membrane (d) containing a plasticizer (e) and filled into two-part, hard gelatin capsules.

Composition G (Enteric-coated Controlled Release Capsule)

Enteric capsules of Composition E can be prepared by coating the controlled-release pellets with 50 mg/capsule of an enteric polymer such as cellulose acetate phthalate, polyvinylacetate phthalate, hydroxypropylmethylcellulose phthalate, or anionic polymers of methacrylic acid and methacrylic acid methyl ester (Eudragit L). Except for Eudragit L, these polymers should also include 10% (by weight of the quantity of polymer used) or a plasticizer to prevent membrane cracking during application or on storage. Suitable plasticizers include diethyl phthalate, tributyl citrate and triacetin.

| (iii) Intravenous injection composition | |
|---|---|
| Active ingredient | 0.200 g |
| Sterile, pyrogen-free phosphate buffer (pH 9.0) to | 10 ml |

The active ingredient is dissolved in most of the phosphate buffer at 35–40° C., then made up to volume and filtered through a sterile micropore filter into sterile 10 ml glass vials (Type 1) which are sealed with sterile closures and overseals.

| (iv) Intramuscular injection composition | |
|---|---|
| Active ingredient | 0.20 g |
| Benzyl Alcohol | 0.10 g |
| Glycofurol 75 | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (Type 1).

| (v) Syrup composition | |
|---|---|
| Active ingredient | 0.25 g |
| Sorbitol Solution | 1.50 g |
| Glycerol | 1.00 g |
| Sodium Benzoate | 0.005 g |

| -continued | |
|---|---|
| (v) Syrup composition | |
| Flavour | 0.0125 ml |
| Purified Water q.s. to | 5.0 ml |

The sodium benzoate is dissolved in a portion of the purified water and the sorbitol solution added. The active ingredient is added and dissolved. The resulting solution is mixed with the glycerol and then made up to the required volume with the purified water.

| (vi) Suppository composition mg/suppository | |
|---|---|
| Active ingredient | 250 |
| Hard Fat, BP (Witepsol H15-Dynamit NoBel) | 1770 |
| | 2020 |

One-fifth of the Witepsol H15 is melted in a steam-jacketed pan at 45° C. maximum. The active ingredient is sifted through a 200 lm sieve and added to the molten base with mixing, using a Silverson fitted with a cutting head, until a smooth dispersion is achieved. Maintaining the mixture at 45° C., the remaining Witepsol H15 is added to the suspension which is stirred to ensure a homogenous mix. The entire suspension is then passed through a 250 lm stainless steel screen and, with continuous stirring, allowed to cool to 40° C. At a temperature of 38–40° C., 2.02 g aliquots of the mixture are filled into suitable plastic moulds and the suppositories allowed to cool to room temperature.

| (vii) Pessary composition | mg/pessary |
|---|---|
| Active ingredient (631 m) | 250 |
| Anhydrous Dextrose | 380 |
| Potato Starch | 363 |
| Magnesium Stearate | 7 |
| | 1000 |

The above ingredients are mixed directly and pessaries prepared by compression of the resulting mixture.

| (viii) Transdermal composition | |
|---|---|
| Active ingredient | 200 mg |
| Alcohol USP | 0.1 ml |
| Hydroxyethyl cellulose | |

The active ingredient and alcohol USP are gelled with hydroxyethyl cellulose and packed in a transdermal device with a surface area of 10 cm$^2$.

Biological Data

The compound of examples 1 and 4 were tested in the radioligand binding assay described herein and were found to have binding affinities of 46.8 and 600 nM respectively.

What is claimed is:
1. A compound of any of the formulae I–XXV:
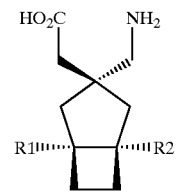
(I)
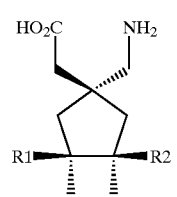
(II)
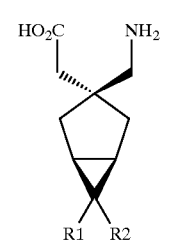
(III)
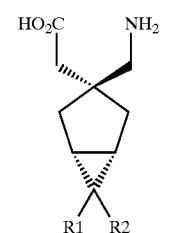
(IV)
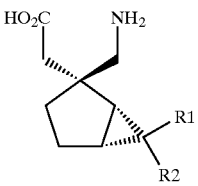
(V)
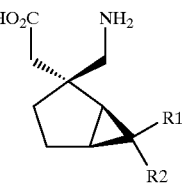
(VI)
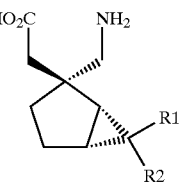
(VII)
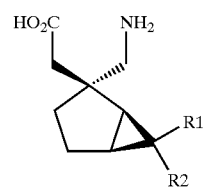
(VIII)
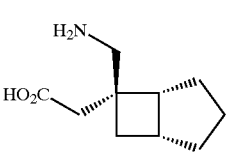
(IX)
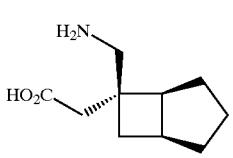
(X)
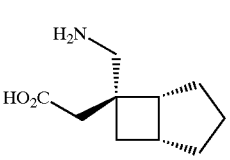
(XI)
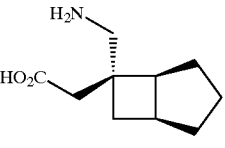
(XII)
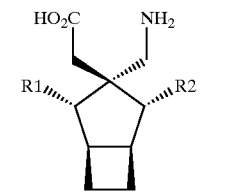
(XIII)
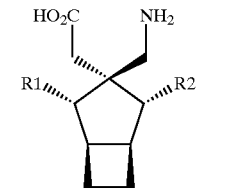
(XIV)
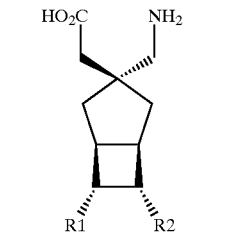
(XV)

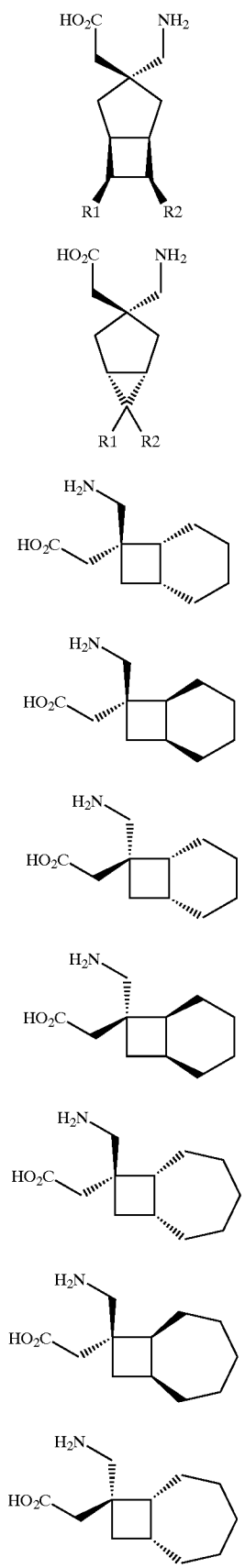

wherein $R^1$ and $R^2$ are each independently selected from hydrogen, straight or branched alkyl of 1–6 carbon atoms, cycloalkyl of from 3–6 carbon atoms, phenyl and benzyl, subject to the proviso that except in the case of a tricyclooctane compound of formula (XVII) $R^1$ and $R^2$ are not simultaneously hydrogen; or a pharmaceutically acceptable salt or solvate thereof; or a prodrug thereof.

2. A compound according to claim 1, wherein $R^1$ and $R^2$ both represent methyl.

3. A compound according to claim 1 or a salt, solvate or prodrug thereof, selected from:

((1R,5S)-3-Aminomethyl-1,5-dimethyl-bicyclo[3.2.0]hept-3-yl)-acetic acid;
((1S,5R)-3-Aminomethyl-1,5-dimethyl-bicyclo[3.2.0]hept-3-yl)-acetic acid;
((1R,5S)-3-Aminomethyl-6,6-dimethyl-bicyclo[3.1.0]hex-3-yl)-acetic acid;
((1S,5R)-3-Aminomethyl-6,6-dimethyl-bicyclo[3.1.0]hex-3-yl)-acetic acid;
((1S,2S,5R)-2-Aminomethyl-6,6-dimethyl-bicyclo[3.1.0]hex-2-yl)-acetic acid;
((1R,2S,5S)-2-Aminomethyl-6,6-dimethyl-bicyclo[3.1.0]hex-2-yl)-acetic acid;
((1S,2R,5R)-2-Aminomethyl-6,6-dimethyl-bicyclo[3.1.0]hex-2-yl)-acetic acid;
((1R,2R,5S)-2-Aminomethyl-6,6-dimethyl-bicyclo[3.1.0]hex-2-yl)-acetic acid;
((1R,5R,6S)-6-Aminomethyl-bicyclo[3.2.0]hept-6-yl)-acetic acid;
((1S,5S,6S)-6-Aminomethyl-bicyclo[3.2.0]hept-6-yl)-acetic acid;
((1R,5R,6R)-6-Aminomethyl-bicyclo[3.2.0]hept-6-yl)-acetic acid;
((1S,5S,6R)-6-Aminomethyl-bicyclo[3.2.0]hept-6-yl)-acetic acid;
cis-((1S,2R,4S,5R)-3-Aminomethyl-2,4-demethyl-bicyclo[3.2.0]hept-3-yl)-acetic acid;
trans-((1S,2R,4S,5R)-3-Aminomethyl-2,4-demethyl-bicyclo[3.2.0]hept-3-yl)-acetic acid;
((1S,5R,6S,7R)-3-Aminomethyl-6,7-dimethyl-bicyclo[3.2.0]hept-3-yl)-acetic acid;
((1S,5R,6R,7S)-3-Aminomethyl-6,7-dimethyl-bicyclo[3.2.0]hept-3-yl)-acetic acid;
((1R,2R,5S)-7-Aminomethyl-3,3-dimethyl-tricyclo[3.3.0.0]oc t-7-yl)-acetic acid:
((1R,6R,7S)-7-Aminomethyl-bicyclo[4.2.0]oct-7-yl)-acetic acid;
((1S,6S,7S)-7-Aminomethyl-bicyclo[4.2.0]oct-7-yl)-acetic acid;
((1R,6R,7R)-7-Aminomethyl-bicyclo[4.2.0]oct-7-yl)-acetic acid;
((1S,6S,7R)-7-Aminomethyl-bicyclo[4.2.0]oct-7-yl)-acetic acid;
((1R,7R,8S)-8-Aminomethyl-bicyclo[5.2.0]non-8-yl)-acetic acid;
((1S,7S,8S)-8-Aminomethyl-bicyclo[5.2.0]non-8-yl)-acetic acid;
((1R,7R,8R)-8-Aminomethyl-bicyclo[5.2.0]non-8-yl)-acetic acid; and ((1S,7S,8R)-8-Aminomethyl-bicyclo[5.2.0]non-8-yl)-acetic acid.

4. A compound according to claim 1 or a salt, solvate or prodrug thereof, selected from:

[(1R,5R,6S)-6-(Aminomethyl)bicyclo[3.2.0]hept-6-yl] acetic acid;
[(1S,5S,6R)-6-(Aminomethyl)bicyclo[3.2.0]hept-6-yl] acetic acid;
[(1RS,5RS,6RS)-6-(Aminomethyl)bicyclo[3.2.0]hept-6-yl] acetic acid;
[(1RS,6RS,7SR)-7-(Aminomethyl)bicyclo[4.2.0]oct-7-yl] acetic acid; and
[(1RS,6RS,7RS)-7-(Aminomethyl)bicyclo[4.2.0]oct-7-yl] acetic acid.

5. A compound according to claim 1 or a salt, solvate or prodrug thereof, which is [(1R,5R,6S)-6-(Aminomethyl)bicyclo[3.2.0]hept-6-yl]acetic acid.

6. A pharmaceutical composition comprising a therapeutically effective amount of a compound according to claim 1 and a pharmaceutically acceptable carrier.

7. A method for treating a disease selected from epilepsy, faintness attacks, hypokinesia, cranial disorders, neurodegenerative disorders, depression, anxiety, panic, pain, irritable bowel syndrome, sleep disorders, osteoarthritis, rheumatoid arthritis, neuropathological disorders, visceral pain, functional bowel disorders, inflammatory bowel diseases, pain associated with dysmenorrhea, pelvic pain, cystitis and pancreatitis, comprising administering a therapeutically effective amount of a compound according to claim 1 to a mammal in need of said treatment.

8. A method according to claim 7 where the disease is neuropathic pain.

9. A process for the preparation of a compound according to claim 1, comprising the steps of:

(i) Acid treatment of the corresponding isocyanate/alkyl of 1–6 carbon atoms carboxylic acid ester derivative;

(ii) Hydrolysis of the corresponding cyclic lactam;

(iii) Reduction of the corresponding nitro/acid derivative, which may be optionally unsaturated; or (iv) Reduction of the corresponding nitro/benzyl or diphenylmethyl ester derivative, which may be optionally unsaturated.

* * * * *